(12) United States Patent
Beaudoin et al.

(10) Patent No.: US 11,439,614 B2
(45) Date of Patent: Sep. 13, 2022

(54) FISH EGG EXTRACTS, OMEGA-3 LIPID-BASED COMPOSITIONS AND USES THEREOF

(71) Applicant: BIOFLASH INC., Rock-Forest (CA)

(72) Inventors: Adrien Beaudoin, Rock-Forest (CA); Luc Beaudoin, St-Joseph-du-Lac (CA)

(73) Assignee: BIOFLASH INC.

( * ) Notice: Subject to any disclaimer, the term of this patent is extended or adjusted under 35 U.S.C. 154(b) by 737 days.

(21) Appl. No.: 15/939,814

(22) Filed: Mar. 29, 2018

(65) Prior Publication Data

US 2018/0280333 A1    Oct. 4, 2018

(30) Foreign Application Priority Data

Mar. 29, 2017   (CA) ................. CA 2962850

(51) Int. Cl.
| | | |
|---|---|---|
| A61K 31/202 | (2006.01) | |
| A23L 33/12 | (2016.01) | |
| A23L 17/30 | (2016.01) | |
| A23L 33/16 | (2016.01) | |
| A23L 33/15 | (2016.01) | |
| A61P 25/28 | (2006.01) | |
| A23L 2/02 | (2006.01) | |
| A23L 2/52 | (2006.01) | |
| A61K 8/36 | (2006.01) | |
| A61K 8/98 | (2006.01) | |
| A61K 31/675 | (2006.01) | |
| A61K 33/06 | (2006.01) | |
| A61K 33/30 | (2006.01) | |
| A61K 33/34 | (2006.01) | |
| A61Q 17/00 | (2006.01) | |
| A61Q 19/00 | (2006.01) | |
| A23C 9/13 | (2006.01) | |
| A23C 9/154 | (2006.01) | |
| A23C 9/156 | (2006.01) | |
| A23C 9/152 | (2006.01) | |
| A23C 9/158 | (2006.01) | |

(52) U.S. Cl.
CPC ......... *A61K 31/202* (2013.01); *A23L 2/02* (2013.01); *A23L 2/52* (2013.01); *A23L 17/30* (2016.08); *A23L 33/12* (2016.08); *A23L 33/15* (2016.08); *A23L 33/16* (2016.08); *A61K 8/361* (2013.01); *A61K 8/987* (2013.01); *A61K 31/675* (2013.01); *A61K 33/06* (2013.01); *A61K 33/30* (2013.01); *A61K 33/34* (2013.01); *A61P 25/28* (2018.01); *A61Q 17/00* (2013.01); *A61Q 19/00* (2013.01); *A23C 9/1315* (2013.01); *A23C 9/1322* (2013.01); *A23C 9/154* (2013.01); *A23C 9/156* (2013.01); *A23C 9/158* (2013.01); *A23C 9/1522* (2013.01); *A23C 9/1528* (2013.01); *A23V 2002/00* (2013.01); *A61K 2800/10* (2013.01)

(58) Field of Classification Search
None
See application file for complete search history.

(56) References Cited

U.S. PATENT DOCUMENTS

| | | | | |
|---|---|---|---|---|
| 8,057,819 | B2* | 11/2011 | Ross | A61P 25/00 424/452 |
| 8,168,611 | B1* | 5/2012 | Perrin | A61K 31/455 514/52 |
| 8,404,875 | B2 | 3/2013 | Beaudoin et al. | |
| 8,535,659 | B1* | 9/2013 | Morrison | A61K 31/525 424/94.1 |
| 2003/0044472 | A1 | 3/2003 | Lang | |
| 2005/0215803 | A1 | 9/2005 | Abril | |
| 2016/0199337 | A1* | 7/2016 | Morris | A61K 31/23 424/93.4 |
| 2016/0278415 | A1 | 9/2016 | Marsland | |
| 2017/0058233 | A1 | 3/2017 | Wang et al. | |

FOREIGN PATENT DOCUMENTS

| | | |
|---|---|---|
| DE | 202007000949 U1 | 5/2007 |
| DE | 202009016672 U1 | 5/2010 |

OTHER PUBLICATIONS

"CDER Conversation: Novel Excipient Review Pilot Program"—https://www.fda.gov/drugs/news-events-human-drugs/cder-conversation-novel-excipient-review-pilot-program#—accessed Jan. 2022.*

Papadopol, V. et al.,"Magnesium and some psychological features in two groups of pupils (magnesium and psychic features)", Magnesium Research (2001) 141(1-2) (Abstract).

Richardson, A.J. et al.,"A randomized double-blind, placebo-controlled study of the effects of supplementation with highly unsaturated fatty acids on ADHD-related symptoms in children with specific learning difficulties", Progress in Neuro-Psychopharmacology & Biological Psychiatry (2002) 26: 233-239.

Serefko, A. et al.,"Magnesium in depression", Pharmacological Reports (2013) 65: 547-554.

(Continued)

*Primary Examiner* — Susan Hoffman

(74) *Attorney, Agent, or Firm* — Lavery, De Billy, LLP; Alain Dumont

(57) ABSTRACT

Novel methods for isolating fish roe/egg extracts, notably a coagulum and a sediment extract, enriched in phospholipids and omega-3 fatty acids are described. Novel compositions comprising omega-3 polyunsaturated fatty acids and micronutrients, which may be used for the management of neurological conditions such as ADD-ADHD, autism, cognitive impairment, and mood disorders are also described. These compositions are homogenous compositions comprising effective amounts of omega-3 fatty acids in microencapsulated or emulsified form, and/or from the sediment extract from fish roe/egg, vitamin B6, magnesium, zinc and copper, and may further comprise additional ingredients such as folic acid (e.g., L-methyl folate) and gamma-linolenic acid (GLA).

26 Claims, 2 Drawing Sheets

(56) References Cited

OTHER PUBLICATIONS

Serfert, Y. et al.,"Sensory Odour Profiling and Lipid Oxidation Status of Fish Microencapsulated Fish Oil", Food Chemistry (2010): 83-110.
Singh, M.N. et al.,"Microencapsulation: A promising technique for controlled drug delivery", Res Pharm Sci. Jul. 2010;5(2) (Abstract).
Sinn, N.,"Nutritional and dietary influences on attention deficit hyperactivity disorder", Nutrition Reviews (2008) 66(10): 558-568.
Sorgi, P.J. et al.,"Effects of an open-label pilot study with high dose EPA/DHA concentrates on plasma phospholipids and behavior in children with attention deficit hyperactivity disorder", Nutrition Journal (2007) 6(16): 1-8.
Starobrat-Hemelin, B. et al.,"The effects of magnesium physiological supplementation on hyperactivity in children with attention deficit hyperactivity disorder (ADHD). Positive response to magnesium oral loading test", Magnes Res (1997) 10(2) (Abstract).
Stevens, L. et al.,"EFA Supplementation in Children with Inattention, Hyperactivity, and other Disruptive Behaviors", Lipids (2003) 38(10): 1007-1021.
Stevens, L. et al., "Essential fatty acids metabolism in boys with attention deficits hyperactivity disorders 1-4", American Journal of Clinical Nutrition (1995) 62:761-768.
Stevenson, J. et al.,"Research review: the role of diet in the treatment of attention-deficit/hyperactivity disorder—an appraisal of the evidence on efficacy and recommendations on the design of future . . . ", Journal of Child Psychology and Psychiatry (2014): 1-12.
Sutcigil, L. et al.,"Pro-and Anti-Inflammatory Cytokine Balance in Major Depression: Effect of Sertraline Therapy", Clinical and Developmental Immunology (2007): 1-6.
Szewczyk, B. et al.,"Antidepressant activity of zinc and magnesium in view of the current hypotheses of antidepressant action", Pharmacological Reports (2008) 60:588-599.
Tiemeier, H. et al.,"Plasma fatty acid composition and depression are associated in the elderly: the Rotterdam Study1-3", The American Journal of Clinical Nutrition (2003) 78:40-46.
Vaisman, N. et al.,"Correlation between changes in blood fatty acid composition and visual sustained attention performance in children with inattention: effect of dietary n-3 fatty acids containing phospholipids1-3", The American Journal of Clinical Nutrition (2008) 87: 1170-1180.
Voigt, R.G. et al.,"A randomized double-blind, placebo-controlled trial of docosahexaenoic acid supplementation in children with attention-deficit/hyperactivity disorder", J Pediatr. Aug. 2001;139(2):189-96 (Abstract).
Wager-Smith, K. et al.,"Depression: A repair response to stress-induced neuronal microdamage that can grade into a chronic neuroinflammatory condition?", Neuroscience & Biobehavioral Reviews (2011) 35(3): 742-764.
Warren E. C. Wacker, and Alfred F. Parisi.,"Magnesium Metabolism", N Engl J Med 1968; 278:772-776 (first 100 words).
Wichers, M. et al.,"The psychoneuroimmuno-pathophysiology of cytokine-induced depression in humans", Internationa Journal of Neuropsychopharmacology (2002) 5: 375-388.
Yorbik, O. et al.,"Potential effects of zinc on information processing in boys with attention deficit hyperactivity disorder", Progress in Neuro-Psychopharmacology & Biological Psychiatry (2008) 32: 662-667.
Ahmad, M. et al.,"Pharmaceutical Microencapsulation Technology for Development of Controlled Release Drug Delivery systems", Journal of Pharmacological and Pharmaceutical Sciences (2011) 5(3): 82-85.
Akhondzadeh, S. et al.,"Zinc sulfale as an adjunct to methylphenidate for the treatment of attention deficit hyperactivity disorder in children: A double blind and randomized trial [ISRCTN64132371]",BMC Psychiatry (2004) 4: 1-6.
Amani, R. et al.,"Correlation Between Dietary Zinc Intakes and Its Serum Levels with Depression Scales in Young Female Students", Biological Trace Element Research (2010) 137:150-158.

Arnold, E. et al.."Does Zinc Moderate Essential Fatty Acid and Amphetamine Treatment of Attention-Deficit/Hyperactivity Disorder?", Journal of Child and Adolescent Psychopharmacol (2000) 10(2) : 111-117.
Belanger, S.A. et al.,"Omega-3 fatty acid treatment of children with attention-deficit hyperactivity disorder: A randomized, double-blind, placebo-controlled study", Paediatrics and Child Health (2009) 14(2): 89-98.
Bernstein, A.L.,"Vitamin B6 in clinical neurology", Annals of the New York Academy of Sciences (1990), Abstract, vol. 585, pp. 250-260.
Bilici, M. et al.,"Double-blind, placebo-controlled study of zinc sulfate in the treatment of attention deficit hyperactivity disorder", Progress in Neuro-Psychopharmacology & Biological Psychiatry (2004) 28 : 181-190.
Calder, P.C.,"n-3 Fatty acids, inflammation and immunity: new mechanisms to explain old actions", Proceedings of the Nutrition Society (2013) 72: 326-336.
Caraci, F. et al., "Targeting Group II Metabotropic Glutamate (mGlu) Receptors for the Treatment of Psychosis Associated with Alzheimer's Disease: Selective Activation of mGlu2 Receptors Amplifies b-Amyloid Toxicity in Cultured Neurons, Whereas Dual Activation of mGlu2 and mGlu3 Receptors Is Neuroprotective", Molecular Pharmacology (2011) 79(3): 618-626.
Dowlati, Y. et al.,"A Meta-Analysis of Cytokines in Major Depression", Biological Psychiatry (2010) 67:446-457.
Edwards, R. et al., "Omega-3 polyunsaturated fatty acids levels in the diet and in red blood cell membranes of depressed patients", Journal of Affective Disorders (1998) 48: 149-155.
Farooqui, A. et al.,"Modulation of inflammation in brain: a matter of fat", Journal of Neurochemistry (2007) 101:577-599.
Freund-Levi, V. et al."w-3 Fatty Acid Treatment in 174 Patients With Mild to Moderate Alzheimer Disease: OmegAD Study", Arch Neurol. (2006) 63: 1402-1408.
Garg, M.L. et al.,"Means of Delivering Recommended Levels of Long Chain n-3 Polyunsaturated Fatty Acids in Human Diets", Journal of Food Science (2006) 71(5): 66-71.
Germano, M. et al.,"Plasma, red blood cells phospholipids and clinical evaluation after long chain omega-3 supplementation in children with attention defict hyperactivity disorder (ADHD)", Nutritional Neuroscience (2007) 10 (1/2): 1-9.
Gow, R. et al.,"Omega-3 fatty acids are related to a abnormal emotion processing in adolescent boys with attention deficit hyperactivity disorder", Prostaglandins Leukotrienes Essential Fatty Acids (2013): 1-11.
Gustafsson, P. et al.,"EPA supplementation improves teacher-rated behavior and oppositional symptoms in children with ADHD", Acta Paediatrica (2010): 1-32.
Haag, M.,"Essential Fatty Acids and the Brain", Canadian Journal of Psychiatry (2003) 48(3):195-203.
Harding, K. et al.,"Outcome-Based Comparison of Ritalin versus Food-Supplement Treated Children with AD/HD", Alternative Medicine Review (2003) 8(3): 319-330.
Held, K. et al.,"Oral Mg2+ Supplementation Reverses Age-Related Neuroendocrine and Sleep EEG Changes in Humans", Pharmacopsychiatry 2002; 35(4): 135-143, Abstract.
Holian, O. et al.,"Action of long-chain fatty acids on protein Kinase C activity: comparison of omega-6 and omega-3 fatty acids", Anticancer Research, May 1, 1992, 12(3):975-980, Abstract.
Houhoula, D. et al.,"A kinetic study of oil deterioration during frying and a comparison with heating", Journal of the American Oil Chemists' Society (2002) 79(2): 133-137.
Huss, M. et al.,"Supplementation of polyunsaturated fatty acids, magnesium and zinc in children seeking medical advice for attention-deficit/hyperactiviy problems—an observation cohort study", Lipids in Health and Disease (2010) 9: 1-12.
Hvas, A.M. et al., "Vitamin B6 Level is Associated with Symptoms of Depression", Psychother Psychosom (2004) 73: 340-343.
Hirayama, S. et al.,"Effect of docosahexaenoic acid-containing food administration on symptoms of attention-deficit/hyperactivity disorder—a placebo-controlled double-blind study", European Journal of Clinical Nutrition (2004) 58: 467-473.

(56) References Cited

OTHER PUBLICATIONS

International Search Report and Written Opinion of corresponding Application No. PCT/CA2018/050390, dated Jun. 28, 2018.
Johnson, M. et al.,"Omega-3/Omega-6 Fatty Acids for Attention Deficit Hyperactivity Disorder", Journal of Attention Disorders (2008): 1-8.
Kidd, P.M.,"Omega-3 DHA and EPA for Cognition, Behavior, and Mood: Clinical Findings and Structural-Functional Synergies with Cell Membrane Phospholipids", Alternative Medicine Review (2007) 12(3): 207-227.
Kolanowski, W. et al., "Sensory Assessment of Microencapsulated Fish Oil Powder", Journal of the American Oil Chemists' Society (2007) 84:37-45.
Kolanowski, W. et al., "Microencapsulation of fish oil by spray drying—impact of oxidative stability. Part 1", European Food Research and Technology (2006): 1-7, Feb. 2006.
Lai, J. et al.,"The efficacy of zinc supplementation in depression : Systematic review of randomised controlled trials", J Affect Disord. Jan. 2012;136(1-2):e31-e39, Abstract.
Lam, P.L. et al.,"Advanced progress of microencapsulation technologies: in vivo and in vitro models for studying oral and transdermal drug deliveries", Journal of Controlled Release Mar. 28, 2014;178:25-45, Abstract.
Latour, A. et al.,"Omega-3 fatty acids deficiency aggravates glutamatergic synapse and astroglial aging in the rat hippocampal CA1", Aging Cell (2013) 12:76-84.
Maes, M. et al.,The inflammatory & neurodegenerative (I&ND) hypothesis of depression : leads for future research and new drug developments in depression, Metabolic Brain Disease (2009) 24:27-53.
Mamalakis, G. et al.,"Depression and adipose essential polyunsaturated fatty acids", Prostaglandins, Leukotrienes and Essential Fatty Acids (2002) 67(5): 311-318.
Mccusker, M. et al.,"Healing fats of the skin: the structural and immunologic roles of the w-6 and w-3 fatty acids", Clinics in Dermatology Jul.-Aug. 2010;28(4):440-51, Abstract.
Milichap, J.J. et al.,"The Diet factor in Attention-Deficit/Hyperactivity Disorder", Pediatrics (2012) 129: 330-338.
Milte, C.M. et al.,"Polyunsaturated fatty acids, cognition and literacy in children with ADHD with and without learning difficulties", Journal of Child Health Care (2011) 15(4) : 299-311.
Moranis, A. et al.,"Long term adequate n-3 polyunsaturated fatty acid diet protects from depressive-like behavior but not from working memory disruption and brain cytokine expression in aged mice", Brain, Behavior, and Immunity (2012) 26: 721-731.
Moreira, J.D. et al.,"Omega-3 fatty acids deprivation affects ontogeny of glutamatergic synapses in rats: relevance for behavior alterations", Neurochem Int. May-Jun. 2010;56(6-7):753-9, Abstract.
Morris, M.C. et al., Consumption of Fish and n-3 Fatty Acids and Risk of Incident Alzheimer Disease, Arch Neurol. (2003) 60:940-946.
Moussain-Bosc, M. et al.,"Magnesium VitB6 Intake Reduces Central Nervous System Hyperexcitability in Children", Journal of the American College of Nutrition (2004) 23(5):545S-548S.
Moussain-Bosc, M. et al.,"Improvement of neurobehavioral disorders in children supplemented with magnesium-vitamin B6 I. Attention deficit hypeactivity disorders". Magnesium Research (2006) 19(1):46-52.
Moussain-Bosc, M. et al.,"Improvement of neurobehavioral disorders in children supplemented with magnesium-vitamin B6 II. Pervasive developmental disorder-autism", Magnesium Research (2006) 19(1):53-62.
Muller, N. et al.,"The immune-mediated alteration of serotonin and glutamate: towards an integrated view of depression". Molecular Psychiatry (2007) 12: 988-1000.
Nechifor, M.,"Magnesium in major depression", Magnesium Research (2009) 22(3): 163S-166S.
Nordic Naturals International Ireland FAQs [online]. Nordic Naturals Inc, 2014. Retrieved from https://www.nordicnaturals.com/ie/faq__ie.php.

\* cited by examiner

Lanes       1      2      3     4

FISH EGG EXTRACTS, OMEGA-3 LIPID-BASED COMPOSITIONS AND USES THEREOF

CROSS REFERENCE TO RELATED APPLICATIONS

The present application claims the benefits of Canadian patent application No. 2,962,850 filed on Mar. 29, 2017, which is incorporated herein by reference in its entirety.

FIELD OF THE INVENTION

The present invention relates to the field of human and animal health and nutrition, and more particularly to compositions for the management of certain diseases and disorders that affect brain function, such as attention-deficit/hyperactivity disorder (ADD-ADHD), depression symptoms and neurodegenerative diseases.

BACKGROUND OF THE INVENTION

Fish roe. In Northern Europe, fish roe is often consumed in a saline solution, with or without smoking. In Asia, Kazunoko (herring roe) well known in Japan, is consumed in a salted preparation. In China, it is eaten after cooking with vapor. In Philippines, herring roe is dried or eaten crude. In many cases the poor conservation conditions favor contamination by microorganisms. In summary, throughout the world, roe is either eaten fresh, or kept in saline, or dried, or smoked or even a combination of these modes. The dietary value of fish eggs is in great part determined by their level of contamination by microorganisms, heavy metals, pesticides, and by their degree of decomposition by enzymes and/or the presence of high concentrations of salt, and finally lipid oxidation. Hence, the quality of roe is highly dependent on temperature, light and oxygen. To this respect, techniques which use heat while keeping the roe in a humid state, at temperatures superior to freezing point, amplify the oxidation phenomenon altering its taste, while giving a characteristic rancid odor. Presence of salt does not protect against oxidation while providing an unwanted level of dietary salt.

Fish roe is rich in phospholipids esterified with high levels of omega-3 fatty acids namely eicosapentaenoic acid (EPA) and docosahexaenoic acid (DHA). There is evidence that these fatty acids are involved in cognitive development of the brain and also disorders which affect the central nervous system namely ADD-ADHD, depression, and neurodegenerative diseases.

Attention deficit with or without hyperactivity (ADD or ADHD) is a disorder that is observed in children, teens and adults. It is characterized by inattention especially persistent and/or hyperactivity-impulsivity occurring more frequently and more severely than generally observed in the population. The American Psychiatric Association (2000) estimated that 3-5% of school-age children are affected by ADHD (DSM-IV), while other sources report a greater frequency ranging from 5 to 13% (L Scahill et al, Schwab-Stone M., 2000); (Boyle et al., 1993); (Breton et al., 1993); (Rowland et al., 2002). It is considered as the most common psychiatric disorder in children.

There are a variety of medications used for the treatment of ADHD and related disorders of attention or activity. These include stimulants, e.g., methylphenidate, dextroamphetamine, Cylert® (pemoline), and modafinil; tricyclic antidepressants, e.g., imipramine and desipramine; selective neuronal norepinephrine uptake inhibitors, e.g., atomoxetine; and/or alpha2 agonists, e.g., clonidine. A number of these medications either have the potential for abuse liability and can produce undesirable side effects (e.g., weight loss, sleep disturbance, cardiac effects, or blood pressure effects) and/or have a delayed onset of action.

Accordingly, there is a need for alternative and/or improved treatment of symptoms associated with ADD-ADHD.

Depression is a mood disorder that causes a persistent feeling of sadness and loss of interest. Also called major depressive disorder or clinical depression, it affects how you feel, think, behave, and can lead to a variety of emotional and physical problems. You may have trouble doing normal day-to-day activities, and sometimes you may feel as if life isn't worth living. Although depression may occur only one time during your life, usually people have multiple episodes of depression. During these episodes, symptoms occur.

Symptoms: Feelings of sadness, tearfulness, emptiness or hopelessness; Angry outbursts, irritability or frustration, even over small matters; Loss of interest or pleasure in most or all normal activities, such as sex, hobbies or sports; Sleep disturbances, including insomnia or sleeping too much; Tiredness and lack of energy, so even small tasks take extra effort; Changes in appetite—often reduced appetite and weight loss, but increased cravings for food and weight gain in some people; Anxiety, agitation or restlessness; Slowed thinking, speaking or body movements; Feelings of worthlessness or guilt, fixating on past failures or blaming yourself for things that aren't your responsibility; Trouble thinking, concentrating, making decisions and remembering things; Frequent or recurrent thoughts of death, suicidal thoughts, suicide attempts or suicide; Unexplained physical problems, such as back pain or headaches.

For many people with depression, symptoms usually are severe enough to cause noticeable problems in day-to-day activities, such as work, school, social activities or relationships with others. Other people may feel generally miserable or unhappy without an identified cause. As in the case of ADD-ADHD, there is also a need for novel approaches for the management of the symptoms of depression.

U.S. Pat. No. 6,541,043 disclose a method and composition for the treatment of attention deficit using dimethylaminoethanol (DMAE), omega 3-fatty acids, betaine, oligomeric proanthocyanidins (OPC), folic acid, vitamins C, E, B12, B6, B5 and beta-carotene, and minerals using lecithin as a source of omega-3 fatty acids. This document does not disclose how the hydrophobic ingredients such as omega 3-fatty acids may be formulated with hydrophilic ingredients such as minerals in a single homogenous composition.

U.S. Pat. No. 7,628,984 describes a formulation for heart and pulmonary health made of two different compositions. It comprises in the first composition B vitamins and minerals, and the second separate composition contains hydrophobic omega-3 lipids and other ingredients such as N-Acetyl Cysteine (NAC), Coenzyme $Q_{10}$ Alpha Lipoic Acid, L-Carnitine and Natural Mixed Carotenoids.

U.S. Pat. No. 8,101,587, as well as related U.S. Pat. Nos. 7,560,123, 8,197,855, 8,609,629 and 8,617,617, describe methods and kits for co-administration of various vitamins and mineral composition. The methods and kits disclosed comprise co-administering one composition comprising vitamin A, beta-carotene, B-complex vitamins, vitamin C, vitamin D3, vitamin E, iron, magnesium and zinc, and a second composition comprising omega-3 fatty acids such as DHA, to supplement the nutritional needs of individuals within physiologically stressful states. The micronutrients (vitamins, minerals) and the omega 3-fatty acids are thus formulated in two distinct compositions.

U.S. Pat. No. 8,362,078 describes a method for reducing the severity of neurological problems using a composition comprising: omega-3 polyunsaturated fatty acids folic acid, vitamin B6 and derivatives thereof, folic acid, zinc and magnesium. The ingredients were incorporated into a chow and administered to rats. This document does not disclose how the hydrophobic ingredients such as omega 3-fatty acids may be formulated with hydrophilic ingredients such as minerals in a single homogenous composition.

Thus, there is a need for the development of novel and improved compositions comprising omega-3 polyunsaturated fatty acids and micronutrients, which may be used for the management of neurological conditions such as ADD-ADHD, neurodegenerative conditions and mood disorders The present description refers to a number of documents, the content of which is herein incorporated by reference in their entirety.

SUMMARY OF THE INVENTION

More specifically, in accordance with the present disclosure, there is provided the following items 1 to 113:
1. A method for the fractionation of fish roe or eggs comprising:
   (a) grinding said fish roe or eggs in the presence of an antioxidant;
   (b) submitting said fish roe or eggs to an osmotic shock at a temperature of less than about 10° C. to obtain a lysed fish roe or eggs mixture;
   (c) sedimenting the mixture obtained in (b) at a temperature of less than about 10° C., thereby obtaining a supernatant fraction and a sediment fraction enriched in phospholipids; and optionally
   (d) saturating the supernatant fraction with a partly miscible solvent to produce a coagulum.
2. A method for obtaining an extract enriched in vitellogenin from fish roe or eggs comprising:
   (a) grinding said fish roe or eggs in the presence of an antioxidant;
   (b) submitting said fish roe or eggs to an osmotic shock at a temperature of less than about 10° C. to obtain a lysed fish roe or eggs mixture;
   (c) sedimenting the mixture obtained in (b) at a temperature of less than about 10° C., thereby obtaining a supernatant fraction; and
   (d) saturating the supernatant fraction with a partly miscible solvent to produce a coagulum, wherein said coagulum is enriched in vitellogenin.
3. A method for obtaining an extract enriched in phospholipids (PLs) esterified with omega-3 polyunsaturated fatty acids from fish roe or eggs comprising:
   (a) grinding said fish roe or eggs in the presence of an antioxidant;
   (b) submitting said fish roe or eggs to an osmotic shock at a temperature of less than about 10° C. to obtain a lysed fish roe or eggs mixture;
   (c) sedimenting the mixture obtained in (b) at a temperature of less than about 10° C., thereby obtaining a sediment fraction enriched in PLs esterified with omega-3 polyunsaturated fatty acids; and optionally:
   (d) drying the sediment fraction of (c).
4. The method of any one of items 1 to 3, wherein said fish roe or eggs are herring, cod, or salmon roe.
5. The method of any one of items 1 to 4, wherein said fish roe or eggs are frozen.
6. The method of any one of items 1 to 5, wherein said grinding is performed using a meat grinder.
7. The method of any one of items1 to 6, wherein said grinding is performed using a grinder disc comprising holes having a diameter of about 4 to 10 mm.
8. The method of item 7, wherein said grinding is performed using a grinder disc comprising holes having a diameter of about 4 to 6 mm.
9. The method of any one of items 1 to 8, wherein said osmotic shock is achieved by incubating said fish roe or eggs in an aqueous solution under agitation.
10. The method of item 9, wherein said aqueous solution is water.
11. The method of item 9 or 10, wherein said incubation is for a period of about 20 to about 40 minutes.
12. The method of any one of items 1 to 11, wherein said temperature is about 0° C. to about 4° C.
13. The method of any one of items 1 to 12, wherein said antioxidant is astaxanthin.
14. The method of any one of items 1 to 13, wherein said partly miscible solvent is a partly miscible alcohol.
15. The method of item 14, wherein said partly miscible alcohol is an aliphatic alcohol comprising at least four carbons.
16. The method of item 15, wherein said partly miscible alcohol is n-butanol or iso-butanol.
17. The method of any one of items 1 to 16, wherein said coagulum is isolated by filtration or decantation.
18. The method of item 17, wherein said coagulum is isolated by filtration on a cheesecloth or metal filter.
19. The method of any one of items 1 to 18, wherein about 20% or more of the lipids comprised in said sediment fraction are phospholipids (PLs) esterified with omega-3 polyunsaturated fatty acids.
20. The method of item 19, wherein about 40% or more of the lipids comprised in said sediment fraction are PLs esterified with omega-3 polyunsaturated fatty acids.
21. The method of any one of items 1 to 20, wherein said sedimenting is for a period of about 30 minutes or more.
22. The method of any one of items 1 to 20, wherein said sedimenting is for a period of about 30 minutes to about 24 hours.
23. The method of any one of items 1 to 22, wherein said method further comprises drying or lyophilizing said coagulum and/or said sediment fraction.
24. The method of item 23, wherein said method further comprises drying or lyophilizing said sediment fraction, wherein said drying is preferably at a temperature of about 40° C. to 60° C.
25. A coagulum obtained by the method defined in any one of items 1 to 23.
26. A cosmetical or cosmeceutical composition comprising the coagulum defined in item 25 and one or more cosmetically acceptable excipients.
27. Use of the coagulum defined in item 25, or the composition defined in item 26, as a moisturizer, as a skin protective agent against free radicals or for the treatment of burns.
28. A food product comprising the coagulum defined in item 25.
29. A sediment extract obtained by the method defined in any one of items 1 to 24.
30. A dried sediment extract from fish roe or eggs comprising at least about 10% or 15% (w/w) of lipids on a dry weight basis.
31. The sediment extract of item 30, comprising about 10 to about 25% (w/w) of lipids on a dry weight basis.

32. The sediment extract of item 30 or 31, wherein at least about 15% of said lipids are phospholipids (PLs).
33. The sediment extract of item 32, wherein about 55% to about 75% of said lipids are PLs.
34. The sediment extract of any one of items 30 to 33, wherein at least 20% of said lipids are esterified by polyunsaturated fatty acids (PUFAs) of the omega-3 type.
35. The sediment extract of item 34, wherein about 25% to about 55% of said PLs are esterified by PUFAs of the omega-3 type.
36. The sediment extract of any one of items 32 to 35, wherein (i) at least about 15% of said PLs are esterified by docosahexaenoic acid (DHA) and/or (ii) at least about 10% of said PLs are esterified by eicosapentaenoic acid (EPA).
37. The sediment extract of item 36, wherein (i) at least about 27-28% of said PLs are esterified by DHA); and/or (ii) at least about 15-16% of said PLs are esterified by EPA.
38. The sediment extract of any one of items 30 to 37, wherein said extract is obtained by the method defined in item 24.
39. An homogenous solid composition comprising: about 50 mg to about 5000 mg of omega-3 fatty acids in solid form; about 10 mg to about 100 mg of vitamin B6; and about 20 mg to about 500 mg of magnesium.
40. The solid composition of item 39, wherein said composition comprises about 100 mg to about 1000 mg of omega-3 fatty acids.
41. The solid composition of item 39, wherein said composition comprises about 300 mg to about 900 mg of omega-3 fatty acids.
42. The solid composition of any one of items 39 to 41, wherein said composition comprises about 20 mg to about 100 mg of vitamin B6, preferably in the form of pyridoxine hydrochloride.
43. The solid composition of any one of items 39 to 41, wherein said composition comprises about 30 mg to about 90 mg of vitamin B6, preferably in the form of pyridoxine hydrochloride.
44. The solid composition of any one of items 39 to 43, wherein said composition comprises about 40 mg to about 300 mg of magnesium, preferably in the form of magnesium picolinate, magnesium glycinate, or magnesium gluconate.
45. The solid composition of any one of items 39 to 43, wherein said composition comprises about 75 mg to about 225 mg of magnesium, preferably in the form of magnesium picolinate, magnesium glycinate, or magnesium gluconate.
46. The solid composition of any one of items 39 to 43, wherein said composition further comprises about 1 mg to about 50 mg of zinc, preferably in the form of zinc picolinate, zinc glycinate, or zinc gluconate; and/or about 0.03 to about 6.5 mg of copper, preferably in the form of copper picolinate, copper glycinate, or copper gluconate.
47. The solid composition of item 46, wherein said composition comprises about 1 mg to about 20 mg of zinc.
48. The solid composition of item 47, wherein said composition comprises about 3.5 mg to about 10.5 mg of zinc.
49. The solid composition of any one of items 46 to 48, wherein said composition comprises about 0.05 mg to about 0.5 mg of copper.
50. The solid composition of any one of items 46 to 49, wherein said composition comprises about 0.1 mg to about 0.3 mg of copper.
51. The solid composition of any one of items 39 to 50, wherein at least a portion of said omega-3 fatty acids are in the form of microencapsulated omega-3 fatty acids.
52. The solid composition of item 51, wherein said microencapsulated omega-3 fatty acids are microencapsulated with gelatin.
53. The solid composition of item 50 or 51, wherein said microencapsulated omega-3 fatty acids are microencapsulated by complex coacervation.
54. The solid composition of any one of items 51 to 53, wherein said omega-3 fatty acids are in the form of microencapsulated omega-3 fatty acids.
55. The solid composition of any one of items 39 to 53, wherein at least a portion of said omega-3 fatty acids are in the form of the sediment defined in any one of items 29 to 38.
56. The solid composition of item 55, wherein said composition comprises about 20 mg to about 200 mg of the sediment defined in any one of items 29 to 38.
57. The solid composition of item 56, wherein said composition comprises about 40 mg to about 150 mg of the sediment defined in any one of items 29 to 38.
58. The solid composition of item 57, wherein said composition comprises about 80 mg to about 120 mg of the sediment defined in any one of items 29 to 38.
59. The solid composition of any one of items 39 to 53, wherein said omega-3 fatty acids comprise docosahexaenoic acid (DHA) and eicosapentaenoic acid (EPA).
60. The solid composition of item 59, wherein said omega-3 fatty acids comprises about 50 mg to about 600 mg of DHA.
61. The solid composition of item 60, wherein said microencapsulated omega-3 fatty acids comprises about 130 mg to about 450 mg of DHA.
62. The solid composition of any one of items 59 to 61, wherein said omega-3 fatty acids comprises about 50 mg to about 600 mg of EPA.
63. The solid composition of item 62, wherein said microencapsulated omega-3 fatty acids comprises about 140 mg to about 500 mg of EPA.
64. The solid composition of any one of items 50 to 54, wherein the DHA/EPA ratio in said omega-3 fatty acids is from about 1/4 to about 4/1, preferably about 2/3 to about 3/2.
65. A container or capsule comprising the solid composition defined in any one of items 39 to 64.
66. The container of item 65, which is an opaque sachet.
67. A liquid composition comprising: about 50 mg to about 5000 mg of omega-3 fatty acids in liquid form; about 10 mg to about 100 mg of vitamin B6; and about 20 mg to about 500 mg of magnesium.
68. The liquid composition of item 67, wherein said composition comprises about 100 mg to about 1000 mg of omega-3 fatty acids.
69. The liquid composition of item 68, wherein said composition comprises about 300 mg to about 900 mg of omega-3 fatty acids.
70. The liquid composition of any one of items 67 to 69, wherein said composition comprises about 20 mg to about 100 mg of vitamin B6, preferably in the form of pyridoxine hydrochloride.
71. The liquid composition of item 70, wherein said composition comprises about 30 mg to about 90 mg of vitamin B6, preferably in the form of pyridoxine hydrochloride.
72. The liquid composition of any one of items 67 to 71, wherein said composition comprises about 40 mg to about 300 mg of magnesium, preferably in the form of magnesium picolinate, magnesium glycinate, or magnesium gluconate.
73. The liquid composition of item 72, wherein said composition comprises about 75 mg to about 225 mg of magnesium, preferably in the form of magnesium picolinate, magnesium glycinate, or magnesium gluconate.
74. The liquid composition of any one of items 67 to 73, wherein said composition further comprises about 1 mg to about 50 mg of zinc, preferably in the form of zinc picolinate, zinc glycinate, or zinc gluconate; and/or about 0.03 to about 6.5 mg of copper, preferably in the form of copper picolinate, copper glycinate, or copper gluconate.
75. The liquid composition of item 74, wherein said composition comprises about 1 mg to about 20 mg of zinc.
76. The liquid composition of item 75, wherein said composition comprises about 3.5 mg to about 10.5 mg of zinc.
77. The liquid composition of any one of items 74 to 76, wherein said composition comprises about 0.05 mg to about 0.5 mg of copper.
78. The liquid composition of item 77, wherein said composition comprises about 0.1 mg to about 0.3 mg of copper.
79. The liquid composition of any one of items 67 to 78, wherein at least a portion of said omega-3 fatty acids are in the form of emulsified omega-3 fatty acids.
80. The liquid composition of item 79, wherein said omega-3 fatty acids are in the form of microencapsulated omega-3 fatty acids.
81. The liquid composition of any one of items 67 to 79, wherein at least a portion of said omega-3 fatty acids are in the form of the sediment defined in any one of items 29 to 38.
82. The liquid composition of any one of items 67 to 81, wherein said omega-3 fatty acids comprise docosahexaenoic acid (DHA) and eicosapentaenoic acid (EPA).
83. The liquid composition of item 82, wherein said omega-3 fatty acids comprises about 50 mg to about 600 mg of DHA.
84. The liquid composition of item 82, wherein said omega-3 fatty acids comprises about 130 mg to about 450 mg of DHA.
85. The liquid composition of any one of items 82 to 84, wherein said emulsified omega-3 fatty acids comprises about 50 mg to about 600 mg of EPA.
86. The liquid composition of item 85, wherein said emulsified omega-3 fatty acids comprises about 140 mg to about 500 mg of EPA.
87. The liquid composition of any one of items 82 to 86, wherein the DHA/EPA ratio in said omega-3 fatty acids is from about 1/4 to about 4/1, preferably about 2/3 to about 3/2.
88. A beverage or food product comprising the composition defined in any one of items 39 to 87.
89. The composition of any one of items 39 to 87, or the beverage or food product of item 88, for use in the improvement of cognitive functions in a subject.
90. The composition, beverage or food product for use according to item 89, wherein said subject suffers from a cognitive impairment.
91. The composition, beverage or food product for use according to item 89 or 90, wherein said subject suffers from attention-deficit/hyperactivity disorder (ADHD), autism or a neurodegenerative condition.
92. The composition, beverage or food product for use according to item 91, wherein said neurodegenerative condition is mild cognitive impairment, Alzheimer's disease or Parkinson's disease.
93. A method for improving cognitive functions in a subject comprising administering to said subject an effective amount of the composition defined in any one of items 39 to 87, or the beverage or food product defined in item 88.
94. The method of item 93, wherein said subject suffers from a cognitive impairment.
95. The method of item 93 or 94, wherein said subject suffers from attention-deficit/hyperactivity disorder (ADHD), autism, or a neurodegenerative condition.
96. The method of item 95, wherein said neurodegenerative condition is mild cognitive impairment, Alzheimer's disease or Parkinson's disease.
97. Use of the composition defined in any one of items 39 to 87, or the beverage or food product defined in item 88, for the improvement of cognitive functions in a subject.
98. The use of item 97, wherein said subject suffers from a cognitive impairment.
99. The use of item 97 or 98, wherein said subject suffers from attention-deficit/hyperactivity disorder (ADHD), autism or a neurodegenerative condition.
100. The use of item 99, wherein said neurodegenerative condition is mild cognitive impairment, Alzheimer's disease or Parkinson's disease.
101. The composition of any one of items 39 to 87, further comprising (i) about 50 mg to about 500 mg of gamma-linolenic acid (GLA) and/or (ii) about 0.1 mg to about 1 mg of folic acid, preferably in the form of L-methylfolate.
102. The composition of item 101, which comprises (i) about 50 mg to about 500 mg of gamma-linolenic acid (GLA) and (ii) about 0.1 mg to about 1 mg of folic acid, preferably in the form of L-methylfolate.
103. The composition of item 101 or 102, wherein said composition comprises about 50 mg to about 400 mg of GLA.
104. The composition of item 103, wherein said composition comprises about 100 mg to about 300 mg of GLA.
105. The composition of any one of items 101 to 104, wherein said composition comprises about 0.2 mg to about 0.8 mg of folic acid, preferably in the form of L-methylfolate.
106. The composition of item 105, wherein said composition comprises about 0.2 mg to about 0.6 mg of folic acid, preferably in the form of L-methylfolate.
107. A beverage or food product comprising the composition defined in any one of items 101 to 106.
108. The composition of any one of items 101 to 106 or the beverage or food product of item 107, for improving a symptom of a mood disorder.
109. The composition, beverage or food product for use according to item 108, wherein said mood disorder is depression or anxiety.
110. A method for improving a symptom of a mood disorder in a subject comprising administering to said subject an effective amount of the composition defined in any one of items 101 to 106 or the beverage or food product of item 107.
111. The method of item 110, wherein said mood disorder is depression or anxiety.
112. Use of the composition defined in any one of items 101 to 106 or the beverage or food product of item 107, for the improvement of a symptom of a mood disorder in a subject.

113. The use of item 112, wherein said mood disorder is depression or anxiety.

In accordance with the present disclosure, there is also provided the following items 1a to 29a:

1a. A method for the fractionation of fish roe or eggs comprising:
(a) grinding said fish roe or eggs in the presence of an antioxidant;
(b) submitting said fish roe or eggs to an osmotic shock at a temperature of less than about 10° C. for at least 20 minutes to obtain a lysed fish roe or eggs mixture;
(c) sedimenting the mixture obtained in (b) at a temperature of less than about 10° C., thereby obtaining a supernatant fraction enriched in vitellogenin and a sediment fraction enriched in phospholipids;
(d) separating the supernatant fraction and sediment fraction by filtration or decantation;
(e) saturating the supernatant fraction with a partly miscible solvent to produce a coagulum;
(f) drying the sediment and coagulum at a temperature of about −30° C. to about 50° C.

2a. The method of item 1a, wherein said fish roe or eggs are herring, cod or salmon roe.

3a. The method of item 1a, wherein said partly miscible solvent is an aliphatic alcohol comprising at least four carbons.

4a. The method of item 1a, wherein about 20% or more of the lipids comprised in said sediment fraction are phospholipids (PLs) esterified with omega-3 polyunsaturated fatty acids.

5a. A coagulum obtained by the method defined in item 1a.

6a. A cosmetical or cosmeceutical composition comprising the coagulum defined in item 5a and one or more cosmetically acceptable excipients.

7a. A method for reducing one or more symptoms of dry skin, skin exposure to free radicals, skin burn or skin wound in a subject, the method comprising topically administering to the subject an effective amount of the coagulum defined in claim 5, or a cosmetical or cosmeceutical composition comprising said coagulum and one or more cosmetically acceptable excipients.

8a. A sediment extract obtained by the method defined in item 1a.

9a. The sediment extract of item 8a, wherein at least 20% (w/w) of said lipids are esterified by polyunsaturated fatty acids (PUFAs) of the omega-3 type.

10a. An homogenous solid composition comprising: about 50 mg to about 5000 mg of omega-3 fatty acids in solid form; about 10 mg to about 100 mg of vitamin B6; and about 20 mg to about 500 mg of magnesium.

11a. The solid composition of item 10a, wherein the composition comprises at least 1000 mg of omega-3 fatty acids; at least 30 mg of vitamin B6; at least 75 mg of elemental magnesium; at least 3.5 mg of zinc in the form of picolinate or glycinate; at least 100 µg of copper in the form of picolinate, glycinate, orotate or gluconate.

12a. The solid composition of item 10a or 11a, wherein at least a portion of said omega-3 fatty acids are in the form of microencapsulated omega-3 fatty acids obtained by complex coarcervation.

13a. The solid composition of item 10a or 11a, wherein said composition comprises about 20 mg to about 200 mg of the sediment defined in item 8a or 9a.

14a. The solid composition of item 10a, wherein said omega-3 fatty acids in solid form comprise about 50 mg to about 600 mg of eicosapentaenoic acid (EPA).

15a. A sachet or capsule comprising the solid composition defined in any one of items 10a to 14a.

16a. A liquid composition comprising: about 50 mg to about 5000 mg of omega-3 fatty acids in liquid form; about 10 mg to about 100 mg of vitamin B6; and about 20 mg to about 500 mg of magnesium.

17a. The liquid composition of item 16a, where the composition comprises at least 1000 mg of omega-3 fatty acids; at least 30 mg of vitamin B6; at least 75 mg of elemental magnesium; at least 3.5 mg of zinc; at least 100 µg of copper in the form of picolinate, glycinate, orotate or gluconate.

18a. The liquid composition of item 16a or 17a, wherein at least a portion of said omega-3 fatty acids are in the form of emulsified or microencapsulated omega-3 fatty acids.

19a. The liquid composition of item 18a, wherein said emulsified omega-3 fatty acids comprise about 50 mg to about 600 mg of eicosapentaenoic acid (EPA).

20a. A beverage or food product comprising the composition defined in any one of items 10a, 11a, 16a and 17a.

21a. A method for improving cognitive functions in a subject in need thereof, the method comprising administering to the subject an effective amount of the composition of any one of items 10a, 11a, 16a and 17a, or a beverage or food product comprising said composition.

22a. The method according to item 21a, wherein said effective amount corresponds to: (a) about 1000 mg of omega-3 fatty acids; about 30 mg of vitamin B6; about 75 mg of elemental magnesium; about 3.5 mg of zinc; and about 100 µg of copper in the form of picolinate, glycinate, orotate or gluconate, for a child, (b) about 2000 mg of omega-3 fatty acids; about 60 mg of vitamin B6; about 150 mg of elemental magnesium; about 7 mg of zinc; and about 200 µg of copper in the form of picolinate, glycinate, orotate or gluconate, for a teenager; and (c) about 3000 mg of omega-3 fatty acids; about 90 mg of vitamin B6; about 225 mg of elemental magnesium; about 10.5 mg of zinc; and about 300 µg of copper in the form of picolinate, glycinate, orotate or gluconate, for an adult.

23a. The method of item 21a or 22a, wherein said subject suffers from a cognitive impairment.

24a. The method of item 22a or 23a, wherein said subject suffers from attention-deficit/hyperactivity disorder (ADHD), autism or a neurodegenerative condition.

25a. The method of item 24a, wherein said neurodegenerative condition is mild cognitive impairment, Alzheimer's disease or Parkinson's disease.

26a. The composition of any one of items 10a, 11a, 16a and 17a, further comprising (i) about 50 mg to about 500 mg of gamma-linolenic acid (GLA) and/or (ii) about 0.1 mg to about 1 mg of folic acid.

27a. A beverage or food product comprising the composition defined of item 26a.

28a. A method for improving a symptom of a mood disorder in an adult subject comprising administering to said subject an effective amount of the composition defined in item 26a, or a beverage or food product comprising said composition.

29a. The method of item 28a, wherein said mood disorder is depression or anxiety.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
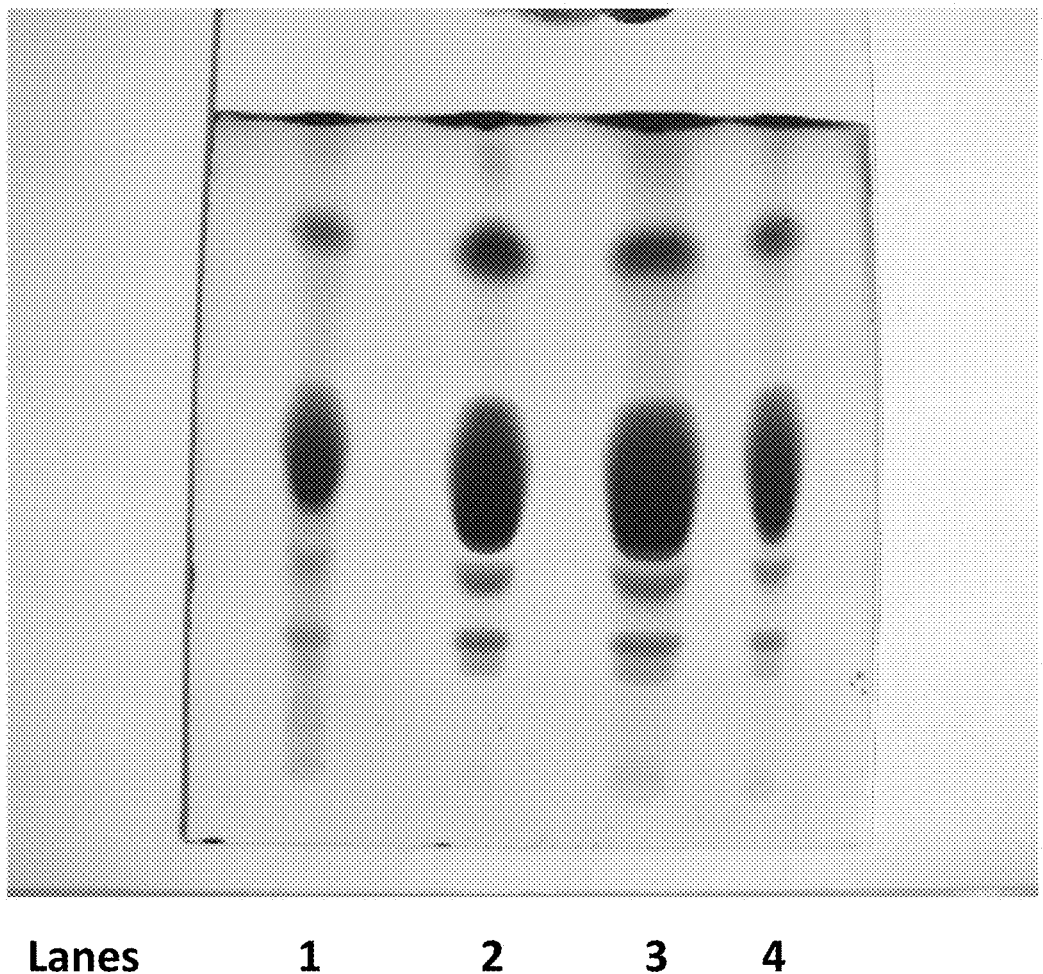
FIG. 1 shows the thin-layer chromatography (TLC) migration pattern of phospholipids in different fractions isolated using the method described herein. Lane 1=supernatant; Lane 2: sediment; Lane 3; whole eggs; Lane 4: coagulum.

Unless otherwise defined, all technical and scientific terms used herein have the same meaning as commonly understood by one of ordinary skill in the art to which this invention belongs.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illustrate the invention and does not pose a limitation on the scope of the invention unless otherwise claimed.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "about" is used to indicate that a value includes an inherent variation of error for the device or the method being employed to determine the value, or encompass values close to the recited values and can refer to a variation of ±10% or 5% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight, volumes, percentages, proximate to the recited range that are equivalent in terms of the functionality of the individual ingredient, the composition, or the embodiment.

The present disclosure relates to the fractionation of fish eggs or roe and the recovery of its components while preserving their integrity. It also relates to the inclusion of these components with other active ingredients in formulas aimed at improving health in certain diseases and disorders which affect brain function, namely the attention deficit (ADD-ADHD), neurodegenerative disorders such as Alzheimer's disease and Parkinson's disease, and mood disorders such as depression. It also relates to an homogeneous combination of hydrophobic ingredients such as omega-3 fatty acids and hydrophilic ingredients such as micronutrients to be administered in a single homogenous preparation.

The method described herein allows a better preservation of the dietary value of roe components. Briefly after freezing, grinding and osmotic shock, the chorionic membrane of the egg is broken and its content is released. A soluble fraction is then separated by settling. The sediment fraction thus obtained, is comprised of two layers of different densities. The fraction is rich in protein and phospholipids (PLs) esterified with omega-3 fatty acids. If the sediment fraction is dried/lyophilised, a stable powder is obtained. The soluble fraction also contains proteins and PLs but in lower amounts. Drying produces a stable fraction from the oxidation viewpoint. Indeed, the peroxide and anisidine values of lipids extracted from these two fractions are very low indicating that there is no significant oxidation after the drying process.

During work on lipid extraction of eggs from various fish species, including herring, (*Clupea harengus*), and salmon, a yellowish color was observed, corresponding to carotenoids, which may explain, at least in part, its good stability. The frozen roe may be passed through a meat grinder and suspended in pure water containing an antioxidant such as astaxanthin. Letting stand the mixture for a few minutes, the solid material sedimented while the yellowish color stays in the semi-transparent supernatant. Separation of the supernatant and centrifugation (e.g., at 5000 g for 15 min) do not yield any precipitate. The crushing of the eggs should be carried out under mild conditions to prevent/minimize emulsification. Indeed, combination of lipoproteins with various classes of lipids, especially PLs, in water represents favorable conditions for emulsification. For example, soft grinding of the semi-frozen eggs with a meat grinder, followed by osmotic shock in water, may be performed, to induce the release of the egg content from its chorionic membrane. To complete the separation of the egg content, the preparation may be submitted to moderate stirring. Egg suspension in ice-cold water may be achieved at various concentrations (10%, 20% or higher concentrations), to obtain a good sedimentation in a relatively short time while avoiding or minimizing physico-chemical and enzymatic transformations. After sufficient agitation (preferably 30 min.), the mixture may be allowed to settle and two fractions are obtained: a semi-transparent yellow supernatant and sediment formed of two parts, a milky and the other grainy. After a certain time (e.g., 30 min), a substantial sedimentation is obtained, which may continue up to 24 hours. The process is ideally performed on ice and in the presence of an antioxidant (astaxanthin) to preserve the integrity of the fractions. The combination of PLs with astaxanthin constitute a powerful antioxidant mixture (see, e.g., U.S. Pat. No. 8,404,875).

In an aspect, the present disclosure provides a method for the fractionation of fish roe or eggs comprising: (a) grinding or crushing of said fish roe or eggs in the presence of an antioxidant; (b) submitting said fish roe or eggs to an osmotic shock at a temperature of less than about 10° C., preferably about 0° C. to about 10° C., about 0° C. to about 8° C., or about 0° C. to about 4° C., to obtain a lysed fish roe or eggs mixture; (c) sedimenting the mixture obtained in (b) at a temperature of less than about 10° C., preferably about 0° C. to about 10° C., about 0° C. to about 8° C., or about 0° C. to about 4° C., thereby obtaining a supernatant fraction and a sediment fraction; and optionally (d) saturating the supernatant fraction with a partly/partially miscible solvent to produce a coagulum.

In another aspect, the present disclosure provides a method for obtaining an extract enriched in vitellogenin from fish roe or eggs comprising: (a) grinding or crushing of said fish roe or eggs in the presence of an antioxidant; (b) submitting said fish roe or eggs to an osmotic shock at a temperature of less than about 10° C., preferably about 0° C. to about 10° C., about 0° C. to about 8° C., or about 0° C. to about 4° C., to obtain a lysed fish roe or eggs mixture; (c) sedimenting the mixture obtained in (b) at a temperature of less than about 10° C., about 0° C. to about 8° C., or about 0° C. to about 4° C., thereby obtaining a supernatant fraction; and (d) saturating the supernatant fraction with a partly/partially miscible solvent to produce a coagulum, wherein said coagulum is enriched in vitellogenin.

The present disclosure also provides a method for obtaining an extract enriched in PLs esterified with omega-3 polyunsaturated fatty acids from fish roe or eggs comprising: (a) grinding or crushing of said fish roe or eggs in the presence of an antioxidant; (b) submitting said fish roe or eggs to an osmotic shock at a temperature of less than about 10° C., preferably about 0° C. to about 10° C., about 0° C. to about 8° C., or about 0° C. to about 4° C., to obtain a lysed fish roe or eggs mixture; (c) sedimenting the mixture obtained in (b) at a temperature of less than about 10° C., preferably about 0° C. to about 10° C., about 0° C. to about 8° C., or about 0° C. to about 4° C., thereby obtaining a sediment fraction enriched in PLs esterified with omega-3 polyunsaturated fatty acids; and optionally: (d) drying the sediment fraction of (c).

Roe or eggs of any fish may be used in the methods described herein (e.g., catfish, menhaden, mackerel, salmon, herring, tuna, shark, haddock, cod, etc.). In an embodiment, the fish roe or eggs are herring, cod or salmon roe or eggs, preferably herring roe or eggs. The fish roe or eggs may be used either fresh or frozen.

The roe or eggs may be grinded or crushed using any suitable systems or devices, for example a meat grinder. The size of the holes of the grinder disc may be adapted by the skilled person to the nature or origin of the eggs/roe being processed. For example, for optimal results with herring roe, the grinding is performed using a grinder disc comprising holes having a diameter of about 4 to about 10 mm, preferably about 4 to about 6 mm.

The grinded or crushed roe or eggs are then subjected to an osmotic shock to induce the release of the egg content from its chorionic membrane, which may be achieved by incubating the fish roe or eggs in a suitable solution, for example an aqueous solution (e.g., water), and preferably under agitation. The incubation is performed for a time sufficient to allow the osmotic shock to occur, for example for at least 5, 10, 15, 20 or 30 minutes. In an embodiment, the incubation is performed for a period of about 10 to about 60 minutes, preferably about 20 to about 40 minutes.

In an embodiment, the mixture may be submitted to moderate stirring. The concentration of the egg or roe (suspension) in the mixture (e.g., with ice-cold water) may be for example at least about 10%, 20% or 30%, or higher concentrations. High concentrations allow to get a good sedimentation in a relatively short time while avoiding or minimizing physico-chemical and enzymatic transformations.

The above-method may be performed in the presence of any suitable antioxidant or combination thereof, for example ascorbic acid, carotenoid (e.g., beta-carotene, astaxanthin), glutathione, butylated hydroxyanisole (BHA), butylated hydroxytoluene (BHT), sodium metabisulfite, propyl gallate or cysteine. In an embodiment, the antioxidant is astaxanthin.

The term "partly/partially miscible solvent" as used herein refers to a solvent that is partly or partially miscible in the supernatant fraction, i.e. wherein mixing the solvent with the supernatant fraction results in a meniscus visible between two layers of liquid, but the volumes and compositions of the layers are not identical to the volumes of the liquids (solvent and supernatant) originally mixed. This contrasts with miscible liquids, wherein mixing the two liquids results in a single liquid phase, and immiscible liquids, wherein mixing the two liquids results in two distinct layers separated by a curved meniscus, with each layer having the same volume and essentially the same composition as the original liquids. In an embodiment, the partly/partially miscible solvent is a partly miscible alcohol, for example an aliphatic alcohol comprising at least four carbons (e.g., from 4 to 8 or 4 to 6 carbons). In a further embodiment, the partly miscible alcohol is n-butanol or iso-butanol.

The coagulum obtained may be isolated by any suitable method for separating heterogenous mixtures (e.g., suspensions), for example by filtration or decantation. In a further embodiment, the coagulum is isolated by filtration, preferably using a cheesecloth or metal filter.

In an embodiment, at least about 15%, 20%, 25%, 30%, 35%, 40% or 45% of the lipids comprises in said sediment fraction are PLs. In an embodiment, up to about 60, 65, 70, 75 or 80% of the lipids comprises in said sediment fraction are PLs.

In an embodiment, the step of sedimenting is performed for a period of at least about 20 or 30 minutes or more, for example for a period of about 30 minutes to about 24 hours, or about 60 minutes to about 12 hours.

In an embodiment, the method further comprises drying or lyophilizing said coagulum and/or said sediment fraction. In an embodiment, the method further comprises drying or lyophilizing said coagulum fraction. In an embodiment, the method further comprises drying or lyophilizing said sediment fraction. Any suitable drying or lyophilisation methods may be used, and the conditions may be determined by the skilled person. To preserve the integrity of the extracts, the drying or lyophilisation is preferably performed at temperatures below about 60° C., e.g. at a temperature of about −30° C. to about 50° C. In an embodiment, the drying is carried out at temperatures of about 20 to about 60° C. or about 40° C. to about 60° C., or by lyophilizing at low temperature (e.g., at about 5° C. or 0° C., or below, for example at a temperature of about 0° C. to about −30° C., −25° C. −20° C., −15° C. or −10° C.).

The Supernatant Fraction (Sub-Fractionation)

It was found that if an alcohol partially miscible with water is added to the soluble fraction, vitellogenin and its lipids form a gelatinous mass. If more alcohol is added, there is formation of an upper phase in which the gelatinous mass migrates. This sub-fraction is a highly hydrated lipoprotein complex referred to herein as a coagulum. This coagulum, which contains lipids, has the property to bind large quantities of water and its lipids are very resistant to oxidation.

The Sediment Fraction

This fraction is rich in PLs bearing the omega-3 polyunsaturated DHA and EPA, the beneficial health properties of which are well known. Moreover, as mentioned above, the lipids present in this fraction are resistant to oxidation. This lipid fraction may be added to preparations aimed at improving cognitive functions and the symptoms of ADD-ADHD, and mood disorders such as depression or anxiety disorders, for example, as described in more detail below.

Lipid Extraction from Eggs of Fish Species

Fish eggs contain high amounts of fat, including PLs. Lipids of salmon and herring eggs contain high levels of omega-3 polyunsaturated fatty acids in an esterified form, namely eicosapentaenoic acid (EPA) and docosahexaenoic acid (DHA). In herring, the lipid content in these fatty acids ranges from 30 to 50% of total fatty acids. Notably, the proportion of PLs in eggs is much higher than in isolated lipids from other fish tissues. Moreover, the stability of isolated herring roe lipids is much better than fish lipids in general, judging by stability studies and oxygen consumption measurements. These observations are corroborated by the formation of propanal during oxidation assays (Moriya et al. 2007). This relative stability may be explained at least in part by the high levels of PLs and presence of carotenoids. (See, e.g., Beaudoin et al., U.S. Pat. No. 8,404,875).

Herring roe properties may apply to other species of fish, as fish eggs exhibit some common biochemical characteristics. Indeed, they all contain vitellogenin and other typical proteins, as well as large amounts of lipids, which serve as energy reserve for the development of the embryo and as structural components of membranes. Hence, high levels of lipids, with PLs constituting a major class, generally constitute more than 30% of the total egg fat. This concentration of PLs is not found in the liver or other fish tissues. Among PLs, phosphatidylcholines (PCs) are the main components (60-80%) whereas phosphatidylethanolamines (PEs) represent significant constituents (5-10%), sphingomyelins (Ss), lysophosphatidylcholines (LysoPCs), phosphatidylserines (PSs) and phosphatidylinositols (PIs) are found in small but measurable quantities. PLs serve as building blocks of biomembranes whereas neutral lipids are used as energy sources. (Prabakhara R. P. G et al, 2014).

Lipids in the supernatant fraction may be measured according to the Bligh and Dyer method (1959). During lipid extraction, when methanol was added to the supernatant fraction, it was noticed that some material aggregated. Similar results were observed with ethanol. When a partly miscible solvent such as n-butanol was added to the same supernatant, a different phenomenon is observed. Indeed, a jellification or coagulation takes place that increased gradually up to the limit of miscibility in the aqueous phase. As more butanol is added, the gelatinous material moved into the butanol upper phase. This coagulum may be easily separated by filtration. Thus, two sub-fractions are obtained from the supernatant: the coagulum and the remaining or "residual" soluble phase. Solid matter (dry weight) and lipid content may be measured in the sediment and the supernatant (sub-fractions). For this purpose, samples are dried on a hot plate at 60° C. overnight and their weight measured by gravimetry. To collect the coagulum from the supernatant, the supernatant is first saturated with n-butanol, and after phase separation, the coagulum, which is in the butanol phase, is filtered through cheesecloth or metal filter, for example. Decantation could also be performed. About 30 g of water per g of dry coagulum is measured. To minimize enzymatic changes and oxidation, it may be desirable to lyophilize the fractions and subfractions instead of drying at high temperatures. The material obtained could then be more easily rehydrated. The gelatinous material may be restored by adding water to the lyophilised material. The coagulate is made of vitellogenin and lipids, comprising PLs esterified with omega-3 polyunsaturated fatty acids such as DHA and EPA. The coagulate exhibits good antioxidant properties and high water binding capacity (see Example 1).

Analysis of Lipid Content.

The method of Bligh and Dyer (1959) may be used. A second extraction of the aqueous phase with an equal volume of chloroform is performed. The two extracts are combined and analyzed. Lipid oxidation is evaluated by measuring peroxide index and anisidine value, using the methods described by Shahidi and Zhong (2005).

Lipid Composition.

PLs may be analysed by separating the different classes by Thin layer chromatography (TLC) on silica gel G™ plates (Silicycle Co., Québec). Samples of the different fractions are loaded on the plate and separated with a mixture of solvents in a chromatography chamber. Migration of lipids may be carried out in: chloroform/methanol/water/acetic acid in a ratio of 65/25/3/4. When migration was completed, lipid spots are detected by exposure to iodine vapor.

Fatty Acid Analysis.

Previous work by Tocher et al. (1985) has shown that fatty acids were present in similar proportions in different PLs. Hence, a fatty acid analysis on the whole roe was performed. For this purpose, lipid roe extract was hydrolysed with hydrochloric acid, and then trans-esterified with boron trifluoride (BF3). The methyl esters of fatty acids obtained were then taken up in 1 ml of dichloromethane and injected on a 10-meter column with 70% cyanopropylpolysilphenylene siloxane as a stationary phase with hydrogen as the carrier gas. Fatty acids esters were determined by chromatographic rapid gas phase (Fast Gas Chromatography). The Supelco™ 37 Component FAME mix was used as an analytical standard for fatty acids. The results reported in the Examples below demonstrate that herring roe lipids are highly enriched in omega-3 polyunsaturated fatty acids, with DHA and EPA representing almost half of total fatty acids of the egg. Polyunsaturated fatty acids of the omega-6 type are at a minimal level. Saturated fatty acids represent nearly 25% of total fatty acids while monounsaturated fats constitute the balance of fatty acids.

Herring roe is vulnerable to contamination by microorganisms when exposed at temperatures higher than 4° C. To limit such contamination, high amounts of salt are typically added. It has the disadvantage of providing an undesirable level of salt not acceptable for many consumers. In the method described herein, there is no salt addition during the separation process. There is a washing step without salt, and the temperature is kept at 4° C. or below. Isolated fractions are dried (e.g., by lyophilisation), and the absence of water limits enzyme transformations and oxidation. The analysis showed that the lipids extracted from the fractions are stable.

In intact unfrozen roe, lipids are vulnerable to oxidation as it is often exposed to light in the presence of water and high temperatures. In the two fractions that were isolated using the methods described herein, these two drawbacks are avoided by dehydration and by adding an effective antioxidant, such as astaxanthin. Brief exposure (e.g., few seconds) of these fractions at temperatures above 60° C. can inhibit enzymatic degradation attributable to endogenous and exogenous enzymes without causing any significant oxidation, as demonstrated by measuring peroxide and anisidine values in the extracted lipids.

The omega-3 fatty acids bearing PLs from both the sediment and supernatant fractions as described above are excellent sources of stable EPA and DHA polyunsaturated fatty acids. The supernatant fraction obtained according to the method described herein contains vitellogenin present as a colloidal suspension. A sub-fraction coagulable by a suitable solvent (n-butanol) has been isolated for the first time. This sub-fraction or coagulate, comprising a lipid and protein complex, can absorb or retain large amounts of water. The combined action of phosvitin, PLs and astaxanthin contribute to confer to the complex antioxidant properties that could be used for example in cosmetic and cosmeceutical applications, notably as a skin protective agent against free radicals or for the treatment of burns. Vitellogenin also contains proteins such as phosvitin which can complex cations, including iron. The chelation or iron may be important to prevent to formation of free radicals and the ensuing oxidation. The coagulum may be used as an antioxidant in food, or hydrating agent in cosmetic and cosmeceutical industries.

Thus, in another aspect, the present disclosure provides a coagulum (comprising lipid and protein complexes) obtained by the method described herein. In an embodiment, the coagulum comprises vitellogenin. In an embodiment, the coagulum comprises phosvitin and PLs. In another embodiment, the coagulum further comprises an antioxidant, e.g., astaxanthin.

In another aspect, the present disclosure provides a cosmetical or cosmeceutical composition comprising the coagulum described herein and one or more cosmetically acceptable excipients or cosmetically acceptable auxiliary agents. The form of the cosmetic composition can be any form normally used for cosmetics such as cream, emulsion, foam, gel, lotion, milk, mousse, ointment, paste, powder, spray, or suspension. The cosmetic composition can be any colored cosmetic used on the skin, hair, eyes, or lips, such as concealing sticks, foundation, stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the claimed compositions can be used in shaving cream (concentrate for aerosol, brushless, lathering), hair groom, cologne stick, cologne, cologne emollient, bubble bath, body lotion (moisturizing, cleansing, analgesic, astringent), after shave lotion, after bath milk and sunscreen lotion. Cosmetically acceptable auxiliary agents include, but are not limited to, carriers, excipients, emulsifiers, surfactants, preservatives, fragrances, perfume oils, thickeners, polymers, gel formers, dyes, absorption pigments, photoprotective agents, consistency regulators, antioxidants, antifoams, antistats, resins, solvents, solubility promoters, neutralizing agents, stabilizers, sterilizing agents, propellants, drying agents, opacifiers, cosmetically active ingredients, hair polymers, hair and skin conditioners, graft polymers, water-soluble or dispersible silicone-containing polymers, bleaches, care agents, colorants, tinting agents, tanning agents, humectants, refatting agents, collagen, protein hydrolyzates, lipids, emollients and softeners, tinting agents, tanning agents, bleaches, keratin-hardening substances, antimicrobial active ingredients, photofilter active ingredients, repellant active ingredients, hyperemic substances, keratolytic and keratoplastic substances, antidandruff active ingredients, antiphlogistics, keratinizing substances, active ingredients which act as antioxidants and/or as free-radical scavengers, skin moisturizing or humectants substances, refatting active ingredients, deodorizing active ingredients, sebostatic active ingredients, plant extracts, antierythematous or antiallergic active ingredients and mixtures thereof.

In another aspect, the present disclosure provides the use of the coagulum or cosmetical/cosmeceutical composition described herein for reducing one or more of the symptoms of a skin condition, e.g., dry skin (e.g., as a moisturizer), skin exposure to radiations (U.V.), skin exposure to sun, skin exposure to free radicals or reactive oxygen species (ROS) (i.e., as a skin protective agent, sunscreen, skin lotion), for reducing signs and symptoms of skin aging, or for the treatment of a skin condition such as burns or wounds.

In another aspect, the present disclosure provides a food composition (e.g., food product) comprising the coagulum described herein. The food composition can be suitable for human or animal consumption. For example, such food compositions/products can be meat products (e.g., processed meats such as sausages, hamburgers, luncheon meats and cold cuts, pre-prepared meat dishes such as meat pies, fish pies, game pies, stews, and other meat-containing dishes, fish products, dairy products, beverage products, baking products, unpasteurized food products, salads, and sauces, marinades, salsas and seasonings.

In another aspect, the present disclosure provides a method for preparing the compositions comprising the coagulum described below, the method comprising (i) obtaining the coagulum by performing the method described herein; and (ii) incorporating the coagulum obtained in the composition, e.g., together with other suitable ingredients such as excipients, food ingredients, etc.

The sediment fraction of the method described herein comprises high concentrations of lipids, more specifically phospholipid esterified with omega-3 polyunsaturated fatty acids, especially DHA and EPA. This concentration may be in the proportion of 45% or more (see Examples below). Thus, this enriched PL preparation may be used in a nutraceutical composition, which may be incorporated into beverages or food products, for example.

Thus, in another aspect, the present disclosure provides a sediment extract (dried or liquid) obtained by the method described herein.

In another aspect, the present disclosure provides a dried sediment extract (e.g., in powder form, lyophilized) from fish roe or eggs comprising at least about 10%, 11%, 12%, 13%, 14%, 15%, 16%, 17%, 18%, 19% or 20% (w/w) of lipids on a dry weight basis. In a further embodiment, the extract comprises about 10%, 11%, 12%, 13%, 14%, or 15% to about 20%, 21%, 22%, 23%, 24% or 25% (w/w) of lipids on a dry weight basis. In an embodiment, at least about 15%, 16%, 17%, 18%, 19%, 20%, 25%, 30%, 35%, 40%, 45%, 50%, 55% or 60% of said lipids are PLs. In a further embodiment, about 20%, 25%, 30%, 35%, 40%, 45% or 50% to about 65%, 70%, 75% or 80%, preferably about 55% to about 75%, of said lipids are PLs. In an embodiment, at least about 20%, 21%, 22%, 23%, 24% or 25% of said lipids are esterified by polyunsaturated fatty acids (PUFAs) of the omega-3 type. In a further embodiment, about 20%, 21%, 22%, 23%, 24% or 25% to about 40%, 45%, 50%, 55% of said lipids are esterified by PUFAs of the omega-3 type.

In an embodiment, at least about 10 to 20% of said lipids are esterified with DHA. In an embodiment, at least about 20%, 21%, 22%, 23%, 24% or 25% of said lipids are esterified by DHA. In an embodiment, at least about 28% of said lipids are esterified by DHA. In a further embodiment, about 20%, 21%, 22%, 23%, 24% or 25% to about 30 or 35% of said lipids are esterified by DHA. In an embodiment, at least about 5%, 6%, 7%, 8%, 9% or 10% of said lipids are esterified by EPA. In an embodiment, at least about 5%, 6%, 7%, 8%, 9% or 10% to about 15%, 16%, 17%, 18%, 19% or 20% of said lipids are esterified by EPA. In another aspect, the present disclosure provides a dried sediment extract (e.g., in powder form, lyophilized) from fish roe or eggs comprising at least about 2%, 3%, 4%, or 5% (w/w) of PLs on a dry weight basis. In an embodiment, the dried sediment extract comprises from about 3% to about 20%, from about 4% to about 18%, or from about 6 to about 16%, of PLs on a dry weight basis.

In an embodiment, the dried sediment extract is obtained by the method described herein.

Figure 2:
FIG. 2 shows a glass of apple juice without (left panel) or with (right panel) the homogenous powder preparation described herein.

This enriched PL fraction of the sediment offers the possibility of combining hydrophobic (lipids such as PLs) with hydrophilic ingredients in a single homogeneous nutraceutical preparation providing an antioxidant system which stabilises the lipids in the formulation. Thus, the present disclosure also relates to novel formulations combining this PL fraction from the sediment fraction as a source long chain polyunsaturated Omega-3 (DHA and EPA) with i) at least one form of the vitamin B6 (Bs vitamers), e.g., pyridoxine, pyridoxamine, pyridoxal, or their phosphorylated derivatives pyridoxine-5'-phosphate, pyridoxal-5'-phosphate, pyridoxamine-5'-phosphate, or any salt thereof (e.g., pyridoxine hydrochloride); ii) magnesium, iii) zinc; and, optionally iv) a source of additional polyunsaturated omega-3 fatty acids forming an homogeneous composition for various applications such treating symptoms of ADHD or ADD, depression and improve cognitive performance. This composition may be used to relieve the symptoms of depression (improving mood, anxiety), autism and neurodegenerative diseases (e.g., Alzheimer's disease), as described below. The composition may be in the form of a powder or a liquid suspension (See FIG. 2).

The present disclosure also relates to an approach for combining active water-soluble ingredients (e.g., micronutrients such as magnesium salt, vitamin B6, zinc salt, etc.) with hydrophobic ingredients such as omega-3 polyunsaturated fatty acids, to form a unique and homogenous composition for various applications, including the treatment individuals suffering from ADD-ADHD syndrome and depression as well as improving memory, anxiety, and mood, as described below. This was made possible by using a microencapsulated form of the omega-3 fatty acids in a powder form, which allows greater stability of the complex relative to a liquid form. Microencapsulation was shown to provide enhanced stability of the fatty acids and resistance to oxidation. Microencapsulation may be performed using various techniques such as spray drying, extrusion, fluid bed drying, extrusion melt injection, complex coacervation, inclusion complexation, liposome entrapment (Kaushik et al.). In the studies described herein, marine lipids omega-3 fatty acids were microencapsulated using complex coacervation technique with fish gelatin in a powder form. The powder preparation can form a homogenous suspension in juices and water, as shown for apple juice in FIG. 2. Materials (typically referred to as "wall materials") suitable for microencapsulation of the omega-3 fatty acids include polymers such as proteins and protein derivatives (e.g., whey proteins, soybean proteins, collagen (e.g., gelatin)), gum arabic, polysaccharides and derivatives thereof (e.g., cellulose-based polymers and derivatives thereof (e.g., cellulose gum, sodium carboxymethyl cellulose, chitin, chitosan), pectin)), and mixtures thereof (e.g., polysaccharide-protein complexes).

Microencapsulation allows to mix hydrophobic with hydrophilic ingredients to obtain a homogeneous composition (e.g., powder) and in a relatively small volume that can be added to beverages and food preparations (juices from fruits and vegetables, smoothies, yogurt, milk and derivatives, as well as resuspension in water).

Thus, in another the present disclosure provide a solid (e.g., powder, lyophilized) homogenous composition comprising: an effective amount of omega-3 fatty acids (e.g., EPA/DHA) in solid form; an effective amount of vitamin B6; and an effective amount of magnesium. In an embodiment, the solid homogenous composition comprises active ingredients consisting of an effective amount of omega-3 fatty acids (e.g., EPA/DHA) in solid form; an effective amount of vitamin B6; and an effective amount of magnesium.

In another aspect, the present disclosure provides a method comprising administering a solid (e.g., powder, lyophilized) homogenous composition comprising: an effective amount of omega-3 fatty acids in solid form; an effective amount of vitamin B6; and an effective amount of magnesium to a subject in need thereof, i.e. a subject in need of supplementation with omega-3 fatty acids, vitamin B6, and magnesium.

In an embodiment, the composition comprises, or consists of, microencapsulated omega-3 fatty acids as the source/form of omega-3 fatty acids. In an embodiment, the composition comprises, or consists of, the sediment fraction/extract described herein as the source/form of omega-3 fatty acids. In an embodiment, the composition comprises microencapsulated omega-3 fatty acids and the sediment fraction/extract described herein as the source/form of omega-3 fatty acids. In a further embodiment, the composition comprises microencapsulated omega-3 fatty acids and the sediment fraction/extract described herein in a ratio of about 10:1 to about 1:10, or about 5:1 to about 1:5, or about 4:1 to about 1:4, or about 3:1 to about 1:3, or about 2:1 to about 1:2 as the source/form of omega-3 fatty acids.

Such a composition is homogenous, which means that the omega-3 fatty acids (e.g., microencapsulated, in the sediment described herein) form an homogenous or uniform mixture with the vitamin B6 and magnesium. In an embodiment, the composition comprises an effective amount of zinc and/or an effective amount of copper, in a further embodiment, the composition comprises an effective amount of zinc and an effective amount of copper.

In an embodiment, the relative amounts (w/w) of omega-3 fatty acids, vitamin B6, magnesium, zinc and copper are as follows: about 55-85%, for example about 70-80%, of omega-3 fatty acids; about 3-12%, for example about 5-10%, of vitamin B6; about 10-30%, for example about 15-20%, of magnesium; about 0.4%-1.5%, for example 0.6-1%, of zinc; and about 0.01 to 0.04%, for example 0.02% to 0.03%, of copper.

The term effective amount as used herein refers to an amount that is sufficient to exert a physiological effect in a subject, e.g., for the improvement of symptoms of ADD-ADHD, cognitive performance/functions, depression (improving mood, anxiety), autism and neurodegenerative diseases (e.g., Alzheimer's disease), as described below. The effective amount is within the following acceptable dosages of mineral and vitamins according to Health Canada monographs:

| Age group (yr) | Mg (mg/d) | B6 (mg/d) | EPA/DHA (mg/d) | Zn (mg/d) | Cu (mg/d) |
| --- | --- | --- | --- | --- | --- |
| 5-8 | 12-110 | 0.05-40 | 100-1500 | 0.4-12 | 0.03-2.5 |
| 9-13 | 12-350 | 0.05-60 | 100-2000 | 0.4-23 | 0.03-4 |

-continued

| Age group (yr) | Mg (mg/d) | B6 (mg/d) | EPA/DHA (mg/d) | Zn (mg/d) | Cu (mg/d) |
|---|---|---|---|---|---|
| 14-18 | 20-350 | 0.1-90 | 100-2500 | 0.7-34 | 0.065-6.5 |
| adult | 20-500 | 0.1-100 | 100-5000 | 0.7-50 | 0.065-8 |

In an embodiment, the amount of magnesium is about 25, 50 or 75 mg to about 300, 400 or 500 mg, for example about 75 mg to about 225 mg.

In an embodiment, the amount of vitamin B6 is about 10, 15 or 20 mg to about 90, 95 or 100 mg, for example about 25 or 30 mg to about 90 or 100 mg.

In an embodiment, the amount of omega-3 fatty acids (e.g., EPA/DHA) is about 30, 50 or 100 mg to about 1000, 2000, 3000, 4000 or 5000 mg, for example about 100 or 200 mg to about 1000, 1500 or 2000 mg, preferably about 250 or 300 to about 900 or 1000 mg. In an embodiment, the DHA/EPA ratio in said omega-3 fatty acids is about 1/4 to 4/1, for example about 1/3 to about 3/1, or about 2/3 to about 3/2.

In an embodiment, the amount of zinc is about 1, 1.5 or 2 mg to about 30, 40 or 50 mg, for example about 2, 2.5 or 3 mg to about 10, 15 or 30 mg, preferably about 3 or 3.5 mg to about 10.5 or 11 mg.

In an embodiment, the amount of copper is about 0.01, 0.02 or 0.03 mg to about 1, 2 or 3 mg, for example about 0.05, 0.06 or 0.07 mg to about 0.5, 0.6 or 0.7 mg, preferably about 0.1 mg to about 0.3 mg.

Any form of the vitamin B6 may be used in the composition (e.g., B6 vitamers), e.g., pyridoxine, pyridoxamine, pyridoxal, or their phosphorylated derivatives pyridoxine-5'-phosphate, pyridoxal-5'-phosphate, pyridoxamine-5'-phosphate, or any physiologically/pharmaceutically acceptable salt thereof (e.g., pyridoxine hydrochloride). In an embodiment, the vitamin B6 is in the form of a physiologically/pharmaceutically acceptable salt, preferably pyridoxine hydrochloride.

The above metals (magnesium, zinc and copper) are available in many forms, including physiologically/pharmaceutically acceptable salts. Suitable physiologically acceptable salts of the above metals with organic acids include salts with orotic acid, aspartic acid, gluconic acid, picolinic acid, tartaric acid, citric acid, lactic acid, acetic acid, fumaric acid, maleic acid, malic acid, ascorbic acid, succinic acid, and amino acids, for example glycine, glutamine or cysteine. In an embodiment, the physiologically/pharmaceutically acceptable salts are picolinate, glycinate and gluconate salts of said metals.

Magnesium is available in many forms, including pharmaceutically acceptable of salts such as magnesium glycinate, magnesium aspartate, magnesium malate, magnesium glutamate, magnesium adipate, magnesium citrate, magnesium orotate, magnesium picolinate, magnesium gluconate, magnesium taurate, magnesium lysinate and magnesium succinate, preferably magnesium picolinate, magnesium glycinate, or magnesium gluconate.

Zinc is available in many forms, including pharmaceutically acceptable zinc salts such as zinc acetate, zinc picolinate, zinc glycinate, zinc gluconate, zinc chloride or zinc citrate, preferably zinc picolinate, zinc glycinate, or zinc gluconate.

Many forms of copper are known to those skilled in the art, including pharmaceutically acceptable copper salts such as cupper orotate, copper gluconate or copper chloride, preferably copper picolinate, copper glycinate, or copper gluconate.

In an embodiment, the composition further comprises one or more additional minerals and/or vitamins. In another embodiment, the composition is free of other minerals and vitamins.

In another embodiment, the omega-3 fatty acids are microencapsulated using a suitable wall material, such as gelatin (e.g., fish gelatin) or any other wall material(s) defined above. In a further embodiment, the omega-3 fatty acids are microencapsulated by complex coacervation.

Non-active secondary ingredients may be added to improve the quality and/or organoleptic properties: antioxidants, aroma, and/or flavors.

In an embodiment, the composition comprises an effective amount of the sediment extract described herein. In an embodiment, the amount of sediment extract in the composition is form about 10, 20, 30, 40 or 50 mg to about 300, 400 or 500 mg, for example from about 20 mg to about 200 mg, about 50 mg to about 150 mg, or about 80 mg to about 120 mg (e.g., about 100 mg). The incorporation of the sediment may be advantageous, for example for the digestion and absorption (bioavailability of the omega-3 fatty acids present in the composition. PLs from the sediment may be digested by intestinal phospholipase A2, secreted by the pancreas, resulting in the formation of 1-acyl lyso-phospholipids and free fatty acids. Lyso-phospholipids have a detergent action and so aid the digestion of other lipids such as the ones which are microencapsulated in the wall material (e.g., in gelatin). The latter is concurrently hydrolysed by proteolytic enzymes secreted by the pancreas. Thus, the hydrolytic products, 1-acyl lyso-phospholipids and free fatty acids, from the sediment may associate with all other products of fat digestion in mixed micelles with bile salts that diffuse to the intestinal mucosa where uptake into the enterocytes occurs. Thus, the addition of sediment may advantageously favor the bioavailability of omega-3 fatty acids.

In an embodiment, the relative amounts (w/w) of microencapsulated omega-3 fatty acids, sediment extract, vitamin B6, magnesium, zinc and copper in the composition are as follows: about 50-70%, for example about 55-65%, of microencapsulated omega-3 fatty acids; about 10-30%, for example about 15-25%, of the sediment extract; about 3-10%, for example about 4-8%, of vitamin B6; about 8-20%, for example about 12-18%, of magnesium; about 0.3%-1.2%, for example 0.5-0.9%, of zinc; and about 0.005 to 0.04%, for example 0.01% to 0.03%, of copper. In an embodiment, the active ingredients present in the composition consists of microencapsulated omega-3 fatty acids, sediment extract, vitamin B6, magnesium, zinc and copper, in the amounts defined above.

The solid composition described herein may be incorporated into capsules, or may be stored into any suitable container (tubes, bottles, sachets), preferably protected from light (opaque container).

Alternatively, one could mix the active hydrosoluble ingredients (vitamin B6, Mg, and optionally Cu and/or Zn) with an emulsion of omega-3 lipids with the same proportions of omega-3 fatty acids. Accordingly, in another aspect, the present disclosure provides a liquid composition comprising omega-3 fatty acids, preferably omega-3 fatty acids in emulsified form; (e.g., EPA/DHA); an effective amount of vitamin B6; and an effective amount of magnesium. In an embodiment, the liquid composition further an effective amount of zinc and/or an effective amount of copper. Emulsion of omega-3 lipids may be prepared using ultrasound or other suitable methods. In an embodiment, the emulsion of omega-3 lipids further comprises an effective amount of an antioxidant, for example a carotenoid (e.g., beta-carotene and/or astaxanthin, preferably beta-carotene). The effective amount of antioxidant may be, for example, from about 0.01, 0.05, 0.01 or 0.5 mM to about 5, 10, 50 or 100 mM, for example from about 0.1 mM to about 10 mM, preferably about 1 mM. Thus, the present disclosure also provides a composition in emulsified form (an emulsion) comprising (i) an effective amount of omega-3 fatty acids; (ii) an effective amount of vitamin B6; and (iii) an effective amount of magnesium. In an embodiment, the composition/emulsion comprises an effective amount of zinc and/or an effective amount of copper, in a further embodiment, the composition/emulsion comprises an effective amount of zinc and an effective amount of copper. The absolute and relative amounts of the ingredients in composition/emulsion are as defined above.

In an embodiment, the composition defined herein further comprises an effective amount of a source of omega-6 fatty acids, for example gamma-linolenic acid (GLA). In an embodiment, the composition defined herein further comprises at least about 20, 30, 40 or 50 mg of GLA, for example about 50, 60, 70, 80, 90 or 100 mg to about 300, 400 or 500 mg of GLA.

In an embodiment, the composition defined herein further comprises an effective amount of a source of folic acid (folate). Folic acid may come in different forms, such as L-methylfolate, levomefolate or methyltetrahydrofolate. In an embodiment, the composition defined herein further comprises an effective amount of L-methylfolate. In an embodiment, the composition defined herein further comprises at least about 0.01, 0.05 or 0.1 mg of folate (e.g., L-methylfolate), for example about 0.01, 0.05 or 0.1 mg to about 1, 2 or 3 mg of folate (e.g., L-methylfolate), preferably about 0.2 to about 0.6 mg, preferably about 0.4 mg.

In an embodiment, the relative amounts (w/w) of microencapsulated omega-3 fatty acids, vitamin B6, magnesium, zinc, copper, GLA and L-methylfolate are as follows: about 50-70%, for example about 55-65%, of microencapsulated omega-3 fatty acids; about 2-10%, for example about 4-8%, of vitamin B6; about 8-20%, for example about 12-16%, of magnesium; about 0.2%-1.2%, for example about 0.5-0.9%, of zinc; about 0.005 to 0.04%, for example about 0.01%-0.03%, of copper; about 0.04% to about 0.15%, for example about 0.06-0.1%, of L-methylfolate; and about 15% to about 25%, for example about 18-22%, of GLA. In an embodiment, the active ingredients present in the composition consists of microencapsulated omega-3 fatty acids, vitamin B6, magnesium, zinc, copper, GLA and L-methylfolate in the amounts defined above.

The solid composition described herein may be incorporated into capsules, or may be stored into any suitable container (tubes, bottles, sachets), preferably protected from light (opaque container).

The composition described herein may be incorporated into a beverage or a food product, such as a juice from fruits and vegetables, a smoothie, a yogurt, milk, milk product, and the like. Accordingly, the present disclosure also provides a beverage or food product comprising the composition described herein.

The composition described herein may be formulated as a gel, for example by mixing it with a thixotropic, thickening or gelling agent. Thus, in another aspect, the present disclosure also provides a gel comprising the composition (liquid) described herein and a thixotropic, thickening or gelling agent. The expression "thixotropic, thickening or gelling agent" refers to agents that can increase the viscosity of a liquid without substantially changing its other properties. Any non-toxic thixotropic, thickening or gelling agent, such as those commonly used in the food and/or cosmetic industry, may be used in the composition described herein. Examples of suitable thixotropic, thickening or gelling agents include thickeners based on polysaccharides such as starches (e.g., arrowroot, cornstarch, katakuri starch, potato starch, sago, tapioca and their starch derivatives), gums (e.g., vegetable gums such as alginin, guar gum, locust bean gum, and xanthan gum), agar, carrageenan, alginic acid, pectin, or proteins (e.g., collagen, egg whites, furcellaran, and gelatin), or polyethylene glycol (PEG), and synthetic polymers (e.g., polyacrylic acid-based polymers).

Fish roe is recognized as an excellent source of lipids enriched in omega-3 polyunsaturated fatty acids. The benefits of omega-3 fatty acids are well known in cardiovascular and neurophysiological systems. There is also evidence that it has some beneficial effects on ADHD, depression and other diseases/disorders related to the central nervous system. Thus, in another aspect, the present disclosure relates to the use of the compositions comprising omega-3 polyunsaturated fatty acids described herein, including fish roe extract, to the management of diseases/disorders related to the central nervous system such as ADD/ADHD, mood disorders (e.g., depression, anxiety), and neurodegenerative conditions such as cognitive impairment, Alzheimer's disease and Parkinson's disease.

Treatment of Symptoms of ADD-ADHD

There is a growing interest on the influence of diet on hyperactivity in childhood. Indeed, researchers found that certain dietary components may have deleterious effects on behavior (A Richardson J., 2000). Interestingly, many physical and behavioral symptoms associated with a fatty acid deficiency (for example, a lack of omega-3 fatty acids) are similar to the symptoms described in typical patients with ADD-ADHD. There is evidence that higher physiological levels of certain omega-3 fatty acids were associated with a decrease in inattention, hyperactivity, emotional problems, conduct problems, and an increase in pro-social behavior, (Kirby et al., 2010).

In addition to lipids containing omega-3 polyunsaturated fatty acids, there are other food ingredients that may improve symptoms of ADD-ADHD. Studies have demonstrated that among individuals suffering from ADD-ADHD, magnesium, zinc and vitamin B6 (in addition to omega-3 fatty acids) are lower than normal on the one hand, and on the other hand, supplementation of each one of these ingredients can separately or in combination (magnesium and vitamin B6 and zinc) improve symptoms of ADD-ADHD (Koziliec et al, 1997; Starobat-Hermelin et al, 1997; Mousain-Bosc et al, 2004; Bilici, 2004; Akhodzadeh et al, 2004; Stevenson et al., 2014; Bhagavan et al. 1975; Mousain Bosc et al., 2006).

EPA and essential fatty acids for ADHD. Attention deficit with or without hyperactivity (ADD or ADHD) is a disorder that is observed in children, teens and adults. It is characterized by inattention especially persistent and/or hyperactivity-impulsivity occurring more frequently and more severely than generally observed in the population. The American Psychiatric Association (2000) estimated that 3-5% of school-age children are affected by ADHD (DSM-IV), while other sources report a greater frequency ranging from 5 to 13%. (L Scahill et al, Schwab-Stone M., 2000); (Boyle et al. 1993); (Breton et al., 1993); (Rowland et al., 2002). It is considered as the most common psychiatric disorder in children. There is a growing interest on the influence of diet on hyperactivity in childhood. Indeed, researchers found that certain dietary components may have deleterious effects on behavior (A Richardson J., 2000). Interestingly, many physical and behavioral symptoms associated with a fatty acid deficiency (for example, a lack of omega-3 fatty acids) are similar to the symptoms described in typical patients with ADHD. It was therefore suggested that perhaps a dietary deficiency of acid omega-3, or an alteration in the metabolic process of these fatty acids would contribute to ADHD. (A J Richardson. 2000). In support of this theory, higher physiological levels of omega-3 were associated with a decrease in inattention, hyperactivity, emotional problems, conduct problems, and an increase in pro-social behavior, (Kirby et al., 2010). Several studies have been conducted to assess and to confirm the hypothesis that omega-3 fatty acids EPA and DHA can treat or prevent ADHD. It was found that a combination of these fatty acids with long chain omega-6 GLA fatty acid leads to a reduction of ADHD symptoms (Transler C., 2010) but it was not sure what were the fatty acids responsible for these effects. A study with 100 boys aged between 6 to 12 years, showed that the frequency of behavioral problems (hyperactivity, impulsivity, conduct disorder, anxiety, access anger and sleep disorders) was associated in children with lower levels of acids omega-3 (L J Stevens. 1996). Administration of fish oil with a high ratio of EPA significantly reduced inattention and hyperactivity in children 4 to 16 years (Germano et al. 2007) while an intake of 360 mg DHA alone, failed to improve the behavior of children aged 6 to 12 years with ADHD (Voigt et al, 2001). In another study with a high ratio of EPA (250 mg EPA and 100 mg DHA), supplementation led to a reduction of symptoms in a subgroup of children with ADHD (Bélanger et al., 2009). A supplement of fish oil with 153 mg EPA and 96 mg DHA improved attention in children 8 to 13 years with reduced visual attention (Vaisman and al., 2008). Another study administered 500 mg of EPA only, to children aged 7 to 12 years with ADHD improved the score of dimensional subscale inattention/cognition of Parent/Teacher Conner's (CTRS) scale. In oppositional children, the total score on the CTRS scales improved in half of children receiving EPA and only 9% of children on placebo (Gustafsson et al., 2010).

A high DHA supplementation in 41 children (8-12 years) with learning difficulties (especially dyslexia) decreased the average score for cognitive disorders and disorders of behavior in general. However, in another study with high intake of DHA, the specific effects of the fatty acid indicated that EPA was rather responsible for improvements in the ADHD. Furthermore, another study found that supplementation with high grade oil DHA had led to no improvement in subjects with ADHD. Indeed, forty children with ADHD took 3.6 grams of DHA per week for a period of 2 months and no significant differences were observed in the attention deficit, hyperactivity, impulsivity, aggression, visual perception, memory for visual and auditory short term, the development of visuo-motor integration or impatience (Hirayama et al., 2004). Johnson et al., 2008) administered fish oil high in EPA to children aged from 8 to 12 and/or 13 to 18 (558 mg EPA, 174 mg DHA, 60 mg of GLA) and noticed up to 50% reduction in the ADHD assessment in some children. And yet in another study, 9 children who received fish oil with a high ratio of EPA (10.8 g EPA and 5.4 g DHA per day) demonstrated significant improvements in their behavior (inattention, hyperactivity, oppositional behavior/provocative, and conduct disorder). There was also a significant correlation between the reduction in arachidonic acid relative to EPA and the level global severity score of the disease. Finally, in the Oxford-Durham study where 580 mg EPA, 174 mg DHA and 60 mg of GLA was administered to children with this disorder. Developmental Coordination (TAC) and major improvements were noted at aggression and behavior. In conclusion, there are many scientific studies that indicate that EPA is responsible for improvements in inattention disorders, hyperactivity and behavior problems. Although few studies have been made with a supplement with high intake of DHA, when DHA was administered there was no significant benefit. It cannot be excluded that GLA offers some benefits considering that some experiments with positive results were carried out with a combination of EPA, DHA and GLA (Richardson. 2002, Sorgi et al., 2007).

There is thus strong evidence that omega-3 fatty acids, notably omega-3 fatty acids of marine origin, are related to emotional control in adolescents who suffer from attention deficit and hyperactivity. This coupled with the fact that children with ADHD have the levels of these fatty acids lower than normal, confirms the role of omega-3 fatty acids, particularly EPA, in the etiology of the disease. These results demonstrated for the first time the relationship between this acid omega-3 fatty acid and emotional problems that accompany the disease. Compositions enriched in omega-3 EPA and DHA, such as herring eggs and the sediment fraction described in this invention thus represent a rich source of omega-3 EPA and DHA, and as a result, can help to correct certain nutritional deficiencies associated with ADHD.

Other food ingredients involved in attention deficit. In addition to lipids containing omega-3 polyunsaturated fatty acids, there are other food ingredients that may improve ADHD. Studies that follow demonstrate that among individuals suffering from ADHD, magnesium, zinc, vitamin B6 and omega-3 fatty acids are lower than normal on the one hand, and on the other hand, supplementation of each one of these ingredients can separately or in combination (magnesium and vitamin B6) can improve the symptoms of ADHD.

Magnesium. In a screening study of 116 children with ADHD, it was observed that 95% of them showed signs of magnesium deficiency (Koziliec et al, 1997). In another clinical trial involving 75 children with ADHD, a daily dose of 200 mg of magnesium for 6 months decreased Hyperactivity as compared to children receiving conventional treatment (Starobat-Hermelin et al, 1997). Attention Deficit also diminished in the magnesium treated group. Impressive results were obtained in hyperactive children by the simultaneous supplementation of magnesium and vitamin B6 (Mousain-Bosc et al, 2004).

Zinc. According to many studies, zinc deficiency is associated with more pronounced symptoms of ADHD. Furthermore, the results of two placebo-controlled trials conducted in Turkey and Iran with 440 children suffering from ADHD indicate that zinc supplementation alone (150 mg of zinc sulfate for 12 weeks, a very high dose) or associated with a conventional drug (55 mg zinc sulfate for 6 weeks) could significantly help children with this condition (Bilici, 2004). According to Dr. E. Arnold of OHIO University, zinc deficiency simulates symptoms of ADHD. Zinc deficiency in children with ADHD was reported as early as 1996 (Akhodzadeh et al, 2004). 43 children between 6 and 16 years (mean 10) were identified as having ADHD were compared with 28 normal same age and sex. The authors concluded that "Zinc is an essential co-factor in a huge number of different processes in the brain and body.". The authors have linked zinc deficiency syndrome "Hyperadrenal" and production of melatonin and serotonin, which both can plausibly contribute to behavioral disturbances observed in ADHD (Stevenson et al., 2014).

Vitamin B6. A vitamin B6 deficiency is at the origin of low levels of neurotransmitters such as Serotonin observed in hyperactive children (Bhagavan et al., 1975). Magnesium and B6 are reciprocally interrelated. Indeed, B6 promotes the absorption of magnesium by the cells, while magnesium is required by alkaline phosphatase for the absorption of vitamin B6 by the tissues. Children with ADHD have inferior levels of magnesium in their red blood cells. A study in children aged 6-7 years showed improvements in behavior: inattention, aggressiveness, hyperactivity after treatment with magnesium and vitamin B6. Amounts administered were 6 mg/kg/day for magnesium and 0.6 mg/kg/day of B6 (Mousain Bosc et al., 2006).

Combination of omega-3 fatty acids, zinc, and magnesium and vitamin 86. The composition described herein represents a combination of several elements including those mentioned above (magnesium and vitamin B6 in addition to omega-3 fatty acids, particularly EPA, and optionally zinc and copper). This may be complemented by the sediment fraction for fish roe/eggs described above which is enriched in PLs bearing omega-3 polyunsaturated DHA and EPA. The homogeneous solid composition described herein combining effective amounts of hydrophilic (zinc, magnesium and vitamin B6) and hydrophobic active ingredients (source of omega-3 fatty acids, such as microencapsulated omega-3 fatty acids, as mixable powder) may thus be used to relieve the symptoms of ADD/ADHD, or other conditions such as autism and Asperger's syndrome.

Improvement of Cognitive Performance/Functions

The monograph associated with fish oils in the database of natural products active ingredients Natural Health Canada allows the use of the claim "contribute to cognitive health and/or brain functions" when the product contains 100-5000 mg EPA+DHA including at least 100 mg of DHA per day. This is supported by the following references: EFSA 2012 Van de Rest et al 2008, Freund-Levi et al. 2006, Fontani et al. 2005, Haag 2003, Morris W T et al. 2003, IOM 2002. Thus, the compositions described herein may be used to improve cognitive functions in subjects, for example subjects suffering from cognitive impairment, including those suffering from neurodegenerative disorders such as Alzheimer's disease, Parkinson's disease, and the like.

Thus, in another aspect, the present disclosure provides a method for improving cognitive functions in a subject comprising administering to said subject an effective amount of the composition, beverage or food beverage described herein. The present disclosure also provides the composition, beverage or food beverage described herein for improving cognitive functions in a subject. The present disclosure also provides the use of the composition, beverage or food beverage described herein for improving cognitive functions in a subject. The present disclosure also provides the use of the composition, beverage or food beverage described herein for the preparation of a medicament for improving cognitive functions in a subject.

Alzheimer's Disease

For several years now, the link between fish oil and Alzheimer's disease has been studied with consistent results. The essential fatty acids vital for brain function that are found in fish oil may not only delay/slow cognitive decline, but may help preventing brain atrophy in older adults. A study looked at the health effects of 4- to 17-month supplementation with omega-3 fatty acids and antioxidants in patients with minor/mild cognitive impairment (MCI), pre-MCI (normal MMSE), and Alzheimer disease (AD) (Fiala et al., The FASEB Journal, vol. 29 no. 7: 2681-2689). The findings confirmed the potential for fish oil to be used as a weapon to fend off the onset of cognitive decline and Alzheimer's disease. Another study examined the relationship between fish oil supplementation and indicators of cognitive decline (Daeillo et al., Alzheimers Dement. 2015 February; 11(2):226-35). The subjects of the study were older adults: 229 cognitively normal individuals, 397 patients with mild cognitive impairment and 193 patients with Alzheimer's disease. They were assessed with neuropsychological tests and brain magnetic resonance imaging every six months while taking fish oil supplements. The study found that the adults taking fish oil (who had not yet developed Alzheimer's and did not have genetic risk factor for developing Alzheimer's known as APOE ε4) experienced significantly less cognitive and brain decline relative to adults not taking fish oil.

A recent study suggests that omega-3 polyunsaturated fatty acids, which are found in fish oil, could improve the function of the glymphatic system, which facilitates the clearance of waste from the brain, and promote the clearance of metabolites including amyloid-β peptides, a primary culprit in Alzheimer's disease (Huixia Ren et al., Omega-3 polyunsaturated fatty acids promote amyloid-β clearance from the brain through mediating the function of the glymphatic system. Published online before print Oct. 7, 2016, doi:10.1096/fj.201600896).

In an embodiment, the subject suffers from a cognitive impairment, for example mild cognitive impairment. In an embodiment, the subject suffers from a neurodegenerative condition, for example Alzheimer's disease or Parkinson's disease. In an embodiment, the subject suffers from ADD/ADHD. In another embodiment, the subject suffers from autism.

Treatment of Symptoms of Mood Disorders

Brain chemistry. When nerve cells communicate with each other in the brain, it involves the release of small signal molecules, the so-called neurotransmitters, which act as chemical messengers in specific points of contact between nerve cells, called synapses. The released neurotransmitter is bound by receptors at the surface of the receiving nerve cell. This will, in turn, trigger a signal which is sent on to other nerve cells. The circuits in the brain using the neurotransmitters noradrenaline, dopamine, GABA and serotonin are known to play an important role in mood, reward and mental well-being, and they also have a key role to in mental disorders such as addiction and depression.

Neurotransmitters levels and depression. It is well known that some cofactors, which affect the enzymes involved in the metabolism of neurotransmitters, influence their levels in the central nervous system. Among these some are related to depression, like magnesium, zinc, vitamin B6 and others. In addition, other factors such as the omega-3 fatty acids, glutamic acids could exert profound influence on the neurotransmitter metabolism and their levels.

Magnesium in depression. A variety of psychiatric symptoms (i.e., hyperexcitability, agitation, tetany, headaches, seizures, ataxia, vertigo, muscular weakness, tremors, irritability, anxiety, insomnia, nervous lipothymias, fatigue, confusion, hallucinations, depression) was observed in magnesium deficiency. All of them were reversible by restoration of normal brain magnesium level (1,2). Apart from malnutrition, low magnesium level in the body may occur due to defects in its absorption or because of its renal loss (for example in case of diabetes, alcoholism, treatment with antidiuretics, aminoglycosides, fluoroquinolones, cisplatin, digoxin, cyclosporine, amphotericin B (3). Acute emotional stress and stressful activities increase magnesium excretion as well (4). Promising preclinical and clinical reports support therapeutic potential of diverse magnesium compositions in different kinds of depression. Antidepressant activity of magnesium was observed after both short-term and chronic administration (references in the review 6,7).

Vitamin 86 and depression. Depression has been associated with deficiency of serotonin or the catecholamines. The synthesis of the serotonin and catecholamines is vitamin B6 dependent, and for this reason vitamin B6 has been considered a therapeutic adjunct in a variety of conditions with known or suspected neurotransmitter abnormalities (8). Besides that, both folate and vitamin B12 appear to facilitate monoamine neurotransmitter synthesis, and thus these vitamins are also suggested to play a role in developing depression. These hypotheses have been supported by the fact that some studies have found low B6 levels (9).

Zinc and Depression. New Zealand has one of the highest rates of mood disorders such as depression in the world. (10). The soil in New Zealand is low in many important nutrients, such as zinc, magnesium, selenium, boron and iodine and this is related to depression and other problems. Zinc is an essential mineral, when your body does not absorb enough, you are more likely to suffer not only from mental health problems (8) particularly depression (11,12,13). A study this year of 402 students found those who had the most zinc in their diet were least likely to have depression (14). The knowledge that low zinc is likely in depression is not new, over 20 years ago zinc levels in the body were found to be lower in people with depression (15). Supplementation of zinc has an antidepressant effect (16-17), it seems to help whether people find pharmaceutical antidepressants helpful or not. Studies have shown zinc influences the chemicals in the brain which are involved in depression (18). Zinc is important to mental health since in the body zinc is found mainly in the brain, so is very important for the health of the nervous system. When zinc is low in the diet several nervous system problems may result including problems with memory, a symptom often experienced with depression. In view of the above, it is not surprising that zinc deficiency is common is the elderly.

Depression and Inflammation. Some new ideas on the causes of depression suggest inflammation in the body could result in less new nerve cells being formed and more nerve cells wearing down. In patients with major depression, low zinc levels appear to be related to increased inflammation (19). In a large study this year found inadequate zinc in the diet of women contributed to depressive symptoms and for those taking pharmaceutical antidepressants supplements of zinc helped relieve their symptoms appears buffer the impact of stress and decrease likelihood of depression.

Omega-3 and depression. Although epidemiological data and clinical trials suggest that omega-3 PUFA may have preventive and therapeutic effects on depression, the underlying mechanisms are still unclear. The protective role of omega-3 fatty acids against depression has been hypothesized to depend on the physiological mechanisms in which fatty acids take part. The pathophysiology of depression has been dominated by the monoamine hypothesis, suggesting that an imbalance, mainly in serotonergic and noradrenergic neurotransmission, is at the core of the pathophysiology of depression. The current therapeutic strategies against depression include drugs which enhance either serotonergic neurotransmission (i.e., selective serotonin reuptake inhibitors (SSRI)), noradrenergic neurotransmission (i.e., noradrenergic reuptake inhibitors (NARI)), or both (i.e., tricyclic antidepressants and more recently serotonin noradrenaline reuptake inhibitors (SNRI)) (20). However, in 30% of the cases, there is little or no response to the medication, and almost half of patients treated with current antidepressant drugs do not show significant clinical improvements (20).

An effect of omega-3 intake suggested to positively influence the depressive status is the potential interaction with the serotoninergic and dopaminergic transmission, including metabolism, release, uptake, and receptor function. The highly unsaturated nature of EPA and DHA provides them with the quality of highly influencing membrane order (namely the fluidity) of several types of cells (21). Omega-3 PUFA also regulate the signal transduction by enhancing G-protein-mediated signal transduction (22,23), membrane-bound enzymes (Na/K-dependent ATPase) (24), and protein kinase C (25). The membrane changing induced by omega-3 PUFA intake may affect different neurotransmitter system altering the regulation of dopaminergic and serotonergic neurotransmission, which are dysfunctional in depressed patients. Changes in serotonin (5-HT) and dopamine receptor (DR-2) number and function caused by changes in PUFA provide the theoretical rationale connecting fatty acids with the current receptor and neurotransmitter theories of depression.

Beside the well-known deficiency in serotonergic neurotransmission as pathophysiological correlate of major depression, recent evidence points out to an important role of increased glutamate receptor activation as well (26). Indeed, an increased activity of the glutamatergic system and N-methyl-D-aspartate (NMDA) receptor agonism has been associated with depressed mood, whereas a reduction of the glutamatergic activity may exert antidepressant action. These effects of the glutamatergic system on mood may depend on its direct or indirect influence on the serotonergic and noradrenergic neurotransmission, since NMDA receptor antagonists increase the serotonin levels in the brain (27, 28). Omega-3 deficiency has been demonstrated to promote age-induced degradation of glutamatergic transmission and its associated astroglial regulation in the hippocampus (29) by slowing astroglial glutamate transport via a specific signal-like effect (30). Further experimental models confirmed that dietary omega-3 content is relevant for the glutamatergic system development and for behavioral performance in adulthood (31). At a molecular level, it has been demonstrated that the NMDA receptor can be stimulated by the protein kinase C, whose conformational changes and optimal activation depend on for membrane content of omega-PUFA (32,33).

Recent studies indicate that factors other than monoamine deficiency or hyperactivation of the HPA axis must be considered when examining the pathogenesis of major depression such as an altered activation of immune system and chronic inflammation with a specific impairment in the signaling of neurotrophins, such as transforming growth factor β1 (TGF-β1) (34,35). According to recent evidence, chronic stress can elicit a neuroinflammatory response through the activation of microglia in CNS, with ensuing release of inflammatory mediators such as interleukin-1β (IL-1β) and tumor necrosis factor-α (TNF-α) (36). The neuroinflammatory response leads to inhibition of neurotrophin signaling and can also elicit both sickness behavior and psychological pain. In addition, chronic stress alters activation of immune system in the periphery, which might account for the state of chronic inflammation observed in depressed patients (37). Different studies have demonstrated a positive correlation between the severity of the symptoms of depression and the increase in the inflammatory status (37). Proinflammatory cytokines interfere with many of the pathophysiological mechanisms that characterize the pathogenesis of depression, altering serotonin metabolism, and reducing both synaptic plasticity and hippocampal neurogenesis (27). On the other hand, reduced levels of anti-inflammatory cytokines, such as interleukin-4 (IL-4), interleukin-10 (IL-10), and TGF-β1, have been found in the plasma of depressed patients (37,38).

Chronic systemic inflammation also contributes to the progression of neurodegeneration (39). The key anti-inflammatory effect of omega-3 fatty acids has been long recognized to depend on their action on eicosanoids. Eicosanoids are biologically active lipid mediators produced from PUFA which play a role in inflammation and regulation of immune function (40). To produce these eicosanoids, AA is released from membrane PLs through the action of phospholipase A2 enzymes and then acts as a substrate for cyclooxygenase (COX), lipoxygenase, or cytochrome P450 enzymes. COX enzymes lead to PG and thromboxanes, lipoxygenase enzymes lead to leukotrienes (LT), and cytochrome P450 enzymes lead to hydroxyeicosatetraenoic and epoxyeicosatrienoic acids. Omega-3 EPA and DHA incorporation in cell membrane decreases their AA content and reduces the amount of substrate available to produce inflammatory and immunoregulatory eicosanoids (41). LTB5, a product of EPA, is a competitive antagonist to LTB4, a highly proinflammatory eicosanoid derived from AA (42). A series of studies gave important information regarding the omega-3 fatty acids as mediators of inflammatory response in depressive status. Indeed, it has been demonstrated that severity of depression varies with the degree of omega-3 fatty acids in erythrocyte membranes, which are decreased in more severe status, as an indicator of oxidative damage (43-46). It has been also reported that plasma fatty acids composition and depression are associated with a significant higher ratio of omega-6 to omega-3 PUFA in depressed subjects (47-50). Many studies also focused on analysis of fasting bloods for detection of plasma fatty acid analysis in risk population. Results from a case-control study conducted on 16 depressed and 22 non-depressed women recruited during the third trimester of pregnancy demonstrated that high DHA, high total n-3, and a low n-6: n-3 ratio were associated with significantly lower odds of depression (51). Similar findings were reported in some studies conducted on depressed postmyocardial infarction (52) and acute coronary syndromes patients (53, 54) in which, compared with control group, lower levels of long-chain omega-3 PUFA as measured by a mean AA/EPA ratio were found. Moreover, a low DEA percentage and low omega-3 proportions of lipid profile predicted risk of suicidal behavior among depressed patients over the 2-year period (55). Other evidences come from a case-control study conducted on 150 subjects reporting an association between fatty acids with serotonergic and immunological markers in depressive patients but not in patients with somatization syndrome suggesting a different biological mechanism of depression and somatoform disorders (56). This may lead to the speculation of a potential bias in previous studies on depression assessment concerning the indiscriminate merging together of both disorders that could affect the outcome. Similarly, an association between omega-3 fatty acids in adipose tissue and major depression has been shown (57-59), although not univocally reported (60,61).

Dysregulation of the functional activity of the immune system in depression is a phenomenon that has been widely reviewed (62). As discussed above, the peripheral immune activation observed in major depression, through the release of proinflammatory cytokines, is responsible for the variety of behavioral, neuroendocrine, and neurochemical alterations that are associated with this psychiatric condition (62). Depression has been associated with excessive production (during an acute phase response) of proinflammatory cytokines, such as IL-1β, IL-12, and interferon-gamma. A recent meta-analysis of experimental studies reported a significantly higher concentration of the proinflammatory cytokines tumor necrosis factor-alpha and IL-6 in depressed subjects compared with control subjects (63). The actions of omega-3 on cells include the changing of the expression of key cell surface proteins and the modulation of the production of proinflammatory cytokines. Indeed, omega-3 PUFA have been reported to decrease production of TNF, IL-1β, and IL-6 in in vitro studies and decrease production of TNF, IL-1β, IL-6, and various growth factors in healthy human subjects, although not all studies confirm this effect (64). At the cellular level, they have been demonstrated to decrease activation of NF-κB, a key transcription factor involved in upregulation of inflammatory cytokine (64). The question arises as to whether the decreased prevalence of depressive symptoms accompanying the higher plasma content of omega-3 PUFA is also associated with improved central inflammation, that is, cytokine activation, in the brain. Recent studies have pointed out the possible role of omega-3 PUFA inducing a central antidepressant-like effect by modulating oxidative reactions and inflammatory cytokine production in microglial and neuronal cells. This determines a reduction of expressions of tumor necrosis factor-α, interleukin-6, nitric oxide synthase, and cyclooxygenase-2, an induction by interferon-γ, and an induction of upregulation of heme oxygenase-1 (HO-1) in BV-2 microglia (65). However, results of experimental studies on cytokines response after administration of omega-3 fatty acids are not univocal. For example, long-term intake of omega-3 increased plasma serotonin concentration and the hippocampus cAMP response element binding protein (CREB) and reducing interleukin-6 (IL-6) expression in rats, but clear dose-dependent effects and significant differences in expressions of IL-1β, tumor necrosis factor-α, brain-derived neurotrophic factors, or phosphorylated CREB were not found (66). Moreover, another experimental study on mice demonstrated that high level of brain DHA was associated with a decrease in depressive-like symptoms throughout aging independently on the cytokines response (in fact, increased interleukin-6 expression and decreased IL-10 expression was found in the cortex of aged mice independently of the diets) (67).

Among the anti-inflammatory actions of omega-3, it is noteworthy that they have been recently discovered as a source of docosanoids, metabolites with a novel stereospecificity unlike that of the known eicosanoids (68). The three known classes, namely, docosatrienes, resolvins, and protectins, are produced mainly from controlled oxidative breakdown of DHA within the membrane and demonstrated anti-inflammatory properties (69). Novel research on depression focused on the role of resolvins, which are thought to terminate ongoing inflammatory cascades and may be responsible for the potential anti-inflammatory effects of omega-3 PUFA in preventing or ameliorating the depressive status (70). Resolvins are grouped into E-series and D-series, depending on if derived by EPA or DHA, respectively. Resolvin E1 has been reported to reduce inflammation by suppressing the activation of the transcription factor nuclear factor-κB and subsequent synthesis of inflammatory cytokines and chemokines (70).

As discussed above, major depression is characterized by increased levels of proinflammatory cytokines and reduced levels of anti-inflammatory cytokines such as IL-10 and TGF-β1. Plasma TGF-β1 levels are reduced in major depressed patients and show a significant negative correlation with the Hamilton Depression Rating Scale (71,72). Interestingly, TGF-β1 levels significantly increase after antidepressant treatment, and SSRI drugs such as sertraline might exert immunomodulatory effects in vivo through a decrease in the proinflammatory cytokine IL-12 and an increase in the anti-inflammatory cytokines such as IL-4 and TGF-β1 (72). Similarly, therapeutic concentrations of venlafaxine prevent microglial activation, reduce proinflammatory cytokine secretion, and finally increase the release of TGF-β1 in an astroglia-microglia coculture model (73). Recent studies suggest that omega-3 fatty acids can increase both in vitro and in vivo the synthesis of TGF-β1 (74, 75) in pregnant women (76), although no studies have been yet conducted in depressed patients. Based on this evidence, it might be worth assessing whether TGF-β1 signaling is a common target both for omega-3 fatty acids and antidepressant drugs, and whether omega-3 fatty acids can exert their antidepressant in vivo effects via the rescue of TGF-β1 signaling. (See a review by Grosso et al. (77)).

Anti-Inflammatory Effects of Gamma Linolenic acid (GLA). GLA is taken up by brain and is converted to prostaglandins such as PGE1, which is a powerful anti-inflammatory product in the central nervous system.

Folic acid. Studies have shown a link between folate deficiency and neuropsychiatric disorders. In particular, depressive symptoms are the most common neuropsychiatric manifestation of folate deficiency (Alpert J E, Fava M. Medscape Psychiatry & Mental Health eJournal. 1997; 2(1)). Folate levels have been found to be inversely associated with depressive symptoms (Beydoun M A, et al., Psychosom Med. 2010; 72(9):862-873) and with longer duration of depressive episodes (Levitt A J, Joffe R T. Biol Psychiatry. 1989; 25(7):867-872). Depressed patients with folate deficiency showed a poorer response to standard treatment with antidepressants (Reynolds E H, Preece J M, Bailey J, et al. Br J Psychiatry. 1970; 117(538):287-292). Therefore, for patients with low plasma or red blood cell folate levels, folate augmentation during antidepressant treatment may improve patient outcomes (Fava M. J Clin Psychiatry. 2007; 68(suppl10):4-7).

Folate is a B vitamin that occurs naturally in food as dihydrofolate and in vitamins and supplements as synthetic folic acid. Dihydrofolate and synthetic folic acid are metabolized in the body into I-5-methyltetrahydrofolate (I-5-MTHF), also known as L-methylfolate, a form of folate that can cross the blood-brain barrier. L-Methylfolate is a cofactor in the production of monoamines serotonin, dopamine, and norepinephrine, which are involved in the regulation of mood and the mechanisms of actions of antidepressants (Stahl S M. CNS Spectr. 2007; 12(10):739-744).

Thus, in another aspect, the present disclosure provides a method for improving symptoms of a mood disorder in a subject comprising administering to said subject an effective amount of the composition, beverage or food beverage described herein. The present disclosure also provides the composition, beverage or food beverage described herein for improving symptoms of a mood disorder in a subject. The present disclosure also provides the use of the composition, beverage or food beverage described herein for improving symptoms of a mood disorder in a subject. The present disclosure also provides the use of the composition, beverage or food beverage described herein for the preparation of a medicament for improving symptoms of a mood disorder in a subject. In an embodiment, the subject suffers from depression (e.g., major depression, post-partum depression, seasonal depression). In another embodiment, the subject suffers from anxiety or an anxiety disorder. In an embodiment, the composition, beverage or food beverage used to improve the symptoms of a mood disorder also comprises GLA. In another embodiment, the composition, beverage or food beverage used to improve the symptoms of a mood disorder also comprises a source of folic acid (e.g., L-methyl folate). In a further embodiment, the composition, beverage or food beverage used to improve the symptoms of a mood disorder comprises GLA and folic acid. In another embodiment, the composition, beverage or food beverage used to improve the symptoms of a mood disorder also comprises inositol.

The total amount of the composition to be administered to a subject may be administered as a single dose or using a fractionated treatment protocol, in which multiple doses are administered over a prolonged period (e.g., once daily, twice daily, etc.). In some embodiments, the composition is administered to the subject daily. In some embodiments, the composition is administered to the subject once per day, twice per day, three times per day, four times per day, or more often. In some embodiments, the composition is administered to the subject once per day, twice per day, three times per day, four times per day, or more often, for a period of 1 day, 2 days, 3 days, 4 days, 5 days, 6 days, 1 week, about 2 weeks, about 3 weeks, about 4 weeks, about 8 weeks, about 12 weeks, about 26 weeks (6 months), or about 52 weeks (1 year).

In an embodiment, the subject to whom the composition, beverage or food product is administered is an animal (e.g., pets, cattle, etc.), preferably a mammal, for example a human.

The present invention is illustrated in further details by the following non-limiting examples.

EXAMPLE 1

Preparation of Various Fractions of Herring Roe/Eggs

The herring roe *Clupea harengus*, caught in the Gaspé region of the Québec province, was passed in a meat-grinder (Cuisinart®) using a disc with average hole size. 125 g of frozen roe was suspended in 875 ml (12.5%) of iced-water containing astaxanthin (0.1 mM) stirred for 30 min (magnetic stirrer), and then allowed to settle at 4° C. The hole diameter of the grinder disc influences sedimentation and should optimally be from about 4 to 10 mm, and preferably 4 to 6 mm. After sedimentation (6 hours), the supernatant was collected and processed for the following determinations: dry matter weight in the supernatant (2.69 g per 100 ml supernatant). Lipid content was estimated by the method of Bligh and Dyer (gravimetry) as described above. 0.277 g of lipids per 100 ml of the supernatant was measured (10.3% on a dry weight basis).

Similarly, the dried weight of the sediment (5.05 g per 100 ml of base) and its fat content (0.944 g 100 ml pellet) were measured. The lipid content of sedimented (pellet) A was estimated at 18.7%. The sediment was incorporated to some of the formulations described below.

To 100 ml of the yellowish supernatant, 30 ml of n-butanol was slowly added, a coagulate formed and separated in an upper phase. The coagulum was dried and 1.72 and weighed 1.72 g/100 ml/2.69 g of dry weight. The non-coagulated part of the supernatant weighed 0.80 g.

The volumes of supernatant and sediment were 650 ml and 350 ml, respectively. The fractions were dried for 24 hours at 60° C. The coagulum has antioxidant properties and high water binding capabilities, as shown below. About 30 g or more of water per g dry weight was measured. For this purpose, the excess water was removed by placing the coagulum in a perforated aluminium container and placed over an adsorbent paper. The container and its content were measured after drying at 50° C. overnight. Lyophilisation produced comparable results. The dried coagulum recovered its gelatinous texture upon rehydration.

An analysis of the lipids was performed. Lipids are present in all the fractions and sub-fractions, however there is lipid enrichment in the sediment fraction. Oxidation values remain very low, indicating good lipid stability in the fractions and sub-fractions (Table 2).

TABLE 2

| Fractions | Dry weight % | Lipids % Fresh weight | Lipids % Dry weight | Peroxydes meq | Anisidine value |
|---|---|---|---|---|---|
| Entire roe | 28 (6) | 4.2 (6) | 14.5 | 1.6 (4) | <1.0 |
| Sediment | 14.0 (2) | 3.0 (2) | 21.4 (2) | 1.6 (2) | <1.0 |
| Supernatant | 14.0 (2) | 1.2 (2) | 8.6 (2) | 1.8 (2) | <1.0 |
| Coagulum of supernatant | 9.5 (2) | 1.1 (2) | 11.6 (2) | — | — |
| Residue of supernatant | 4.6 (2) | 0.15 (2) | 3.2 (2) | — | — |

Dry weight: mass obtained after drying (the entire roe represents 28 g/100 g of initial mass)
Lipids (fresh weight): g/100 g of fresh weight
Lipids (dry weight): g/100 g of dry weight
Peroxyde value: measure of the extent to which an oil has undergone primary oxidation, expressed as milliequivalents (meq). It represents the amount of peroxide oxygen per kg of fat and oil. Target should be below 5.
Anisidine value: aldehydes, derived from secondary oxidation of fat and oils, react with the p-anisidine, determining a variation of absorbance at 350 nm.

PLs in the total roe extract represent about 66% of the lipids. The different classes of lipids were determined by the Iatroscan method. FIG. 1 shows the PLs migration pattern on TLC. Similar patterns were found in fractions and subfractions, indicating first an homogeneity in PL classes distribution and second that very little lipid hydrolysis occurred during the extraction.

The sediment obtained comprises concentrations of fortified PLs esterified polyunsaturated fatty acids of the omega-3 type in a proportion of about 45% or more (Table 3). The PL content was of the order of about 66% of the lipids from the sediment, which form about 21.5% of dry weight basis, which is equivalent to 14% PL/g of the dried sediment (i.e. 140 mg of PLs per g of sediment), which is higher than the phospholipid content of krill (35% of total PL, that form 12% of fat on a dry weight basis, corresponding to 4.2% PL/g. Krill lipid concentrations are estimated on the basis of commercial products: NKO™ from Neptune Technologies Bioresources; while the total fat in the dry weight of krill are based on Krilex™ from Medelys Laboratories International Inc.

TABLE 3

Fatty acid composition (%) of the sediment obtained from herring roe lipids

| Fatty acid | Replicate 1 | Replicate 2 | Replicate average |
|---|---|---|---|
| C8:0 | nd | nd | nd |
| C10:0 | 0.102 | 0.101 | 0.101 |
| C11:0 | nd | nd | nd |
| C12:0 | 0.012 | 0.013 | 0.012 |
| C13:0 | 0.012 | 0.012 | 0.012 |
| C14:0 | 3.795 | 4.007 | 3.901 |
| 14:1 | 0.197 | 0.206 | 0.201 |
| C15:0 | 0.613 | 0.620 | 0.617 |
| C15:1 | 0.157 | 0.140 | 0.149 |
| C16:0 | 20.832 | 20.984 | 20.908 |
| C16:1 | 4.594 | 4.847 | 4.720 |
| C17:0 | 0.278 | 0.278 | 0.278 |
| C17:1 | 0.286 | 0.310 | 0.298 |
| C18:0 | 1.738 | 1.768 | 1.753 |
| C18:1 n9t | 0.036 | 0.036 | 0.036 |
| C18:1 n9c | 8.903 | 9.918 | 9.410 |
| C18:2 n6 | 0.005 | 0.005 | 0.005 |
| C18:2 n6 | 0.797 | 0.864 | 0.831 |
| C18:3 n6 | 8.903 | 9.918 | 9.410 |
| C18:3 n3 | 0.005 | 0.005 | 0.005 |
| C20:0 | 0.865 | 0.897 | 0.881 |
| C20:1 n9 | 3.525 | 3.881 | 3.703 |
| C20:2 | 0.123 | 0.144 | 0.133 |
| C21:0 | nd | nd | nd |
| C20:3 n6 | 0.022 | 0.048 | 0.035 |
| C20:4 n6 | 0.398 | 0.392 | 0.395 |
| C20:3 n3 | 0.064 | 0.066 | 0.065 |
| C22:0 | 0.567 | 0.605 | 0.586 |
| C20:5 n3 (EPA) | 16.247 | 15.862 | 16.054 |
| C22:1 n9 | nd | nd | nd |
| C22:1 n9 | nd | nd | nd |
| C22:2 | 0.053 | 0.051 | 0.052 |
| C23:0 | 0.001 | 0.001 | 0.001 |
| C24:0 | nd | nd | nd |
| C24:1 | 2.078 | 2.045 | 2.062 |
| C22:6 n3 (DHA) | 30.612 | 28.822 | 29.717 |
| Unknowns A, B, C | 0.60 | 0.57 | 0.57 |
| Unknown D | 1.761 | 1.701 | 1.731 |
| Σ AGS | 28.813 | 29.286 | 29.050 |
| Σ AGM | 19.777 | 21.382 | 20.579 |
| Σ AGP | 49.052 | 47.055 | 48.053 |
| Σ Unknowns | 2.358 | 2.277 | 2.318 |
| Total n-3 | 47.615 | 45.501 | 46.558 |
| Total n-6 | 1.262 | 1.359 | 1.310 |
| Ratio n3/n6 | 49.052 | 47.055 | 48.053 |

SFA: Saturated fatty acids;
MFA: Monounsaturated fatty acid;
PFA: Polyunsaturated fatty acid

EXAMPLE 2

Preparation of Various Fractions of Salmon Roe

Farmed salmon roe was used and the same process as described in Example 1 was performed to determine if a supernatant and a sediment could be obtained. Salmon eggs were bigger and more colored (red) than herring eggs. A supernatant and a sediment were obtained, and the sediment was used for preparation B of table 7 (Example 4).

EXAMPLE 3

Preparation of a Representative Composition Using the Sediment Fraction

A representative food or nutraceutical composition for human consumption was produced using the sediment obtained by the process described in Example 1. This composition was designed to meet Health Canada standards. The composition comprises the following ingredients (Table 4):

TABLE 4

| Ingredient | Amount (teaspoon) |
|---|---|
| Sediment fractionation process fish eggs | 100 mg |
| ethylated fatty acids DHA and EPA | 134 mg DHA |
| | 153 mg EPA |
| Vitamin B6 | 30 mg |
| Magnesium | 75 mg |
| Zinc | 3.5 mg |
| Copper | 100 µg |
| Beta-cyclodextrin | 50 mg |
| Natural flavors (fruit extract) | 25 mg |

The recommended doses of the composition to attenuate the symptoms of ADHD are: 1 teaspoon per day for children aged 5-8 years inclusively, 2 teaspoons per day for children aged 9-13 years, and 3 teaspoons per day for teens aged 14-18 years and adults.

EXAMPLE 4

Preparation of Different Compositions Comprising Omega-3 Fatty Acids

Until now, it has been a challenge to formulate preparations containing hydrophobic omega-3 fatty acids (e.g., EPA) with micronutrients such as minerals and vitamins because of the different physicochemical properties of these ingredients. Hydrophobic lipids omega-3 fatty acids could not be mixed with water soluble hydrophilic micronutrients. Also, oxidation is another factor that must be considered when mixing lipids in an hydrophilic medium because water favors lipid oxidation and the bad odor and taste that ensues.

In order to mix these ingredients in a homogeneous preparation, the following approaches were considered in the present work.

1) Emulsion. For the preparation of a liquid formulation, vitamin B6 and minerals were solubilised and lipids were mixed as an emulsion with ultrasounds. Some instability in the long term and lipid oxidation (TOTOX values superior to 20) were observed in the initial tests. However, addition of an antioxidant (beta-carotene) was shown to significantly improve the physicochemical properties, notably the lipid oxidation, of the formulation.

2) Gel suspension. Lipids, as ethyl esters, were combined with cyclodextrin and then suspended in water solution containing a thixotropic agent, Xanthan gum. As shown in table 6 below, the preparation was prone to oxidation with the development of unpleasant fish taste and odor in the long term.

3) Microencapsulation/complexation of lipids. Three distinct preparations were tested.

Preparation C: Omega-3 lipids were complexed with a cage molecule (Beta-cyclodextrin) to make a powder that could be mixed with the other active ingredients (vitamins and minerals) in a solid state form. For this purpose, the ethyl esters EPA:DHA were suspended in ethanol and added to beta-cyclodextrin. Ethanol was evaporated under nitrogen at low temperature. The complex was thoroughly mixed with the solid ingredients and sealed in 5 g sachets protected by aluminum lining.

Preparation D: Microencapsulated polyunsaturated omega-3 lipids in a solid state (powder format, DSM Nutritional Products, Inc.) was thoroughly mixed with the other active ingredients (vitamins and minerals) in a solid state form together with dried herring roe fraction (sediment) described herein.

Preparation E: Microencapsulated polyunsaturated omega-3 fatty acids in a solid state was thoroughly mixed with the other active ingredients (vitamins and minerals) as Preparation D, and the mixture was sealed in 5 g sachets protected by aluminum lining.

These preparations were tested for homogeneity (I) and oxidation (II).

I) Homogeneity

To assess the homogeneity of the preparations, the sachet content was weighed and the lipid fraction was extracted by adding 10 ml of 1:1 Chloroform:Methanol (V/V), followed by centrifugation at 1000×g for 3 min. The supernatant was carefully decanted, evaporated and weighed. In parallel, homogeneity of the preparations was assessed by measuring magnesium by atomic absorption spectrometry on samples taken at random in the preparation. The results are presented in Table 5 below, and show that the different preparations are homogenous since the measured $Mg^{2+}$ weights in the samples were consistent with the expected $Mg^{2+}$ weight of 30 mg/g. In the case of preparations D and E, a fraction of the lipid protein-complex floated on the surface of the solvent, although this has no effect on the homogeneity of these preparations.

TABLE 5

Homogeneity of the preparations

| | Solvent extractibles | | | $Mg^{2+}$ weight | | |
|---|---|---|---|---|---|---|
| Preparations | Number of samples | % of total Mean | S.D. | Number of samples | mg/g Mean | S.D. |
| C | 10 | 8.8 | 1.19 | 6 | 28.8 | 3.48 |
| D | 10 | 60.1 | 2.24 | 6 | 30.7 | 1.63 |
| E | 10 | 58.6 | 3.23 | 6 | 29.7 | 2.86 |

Note:
The expected $Mg^{2+}$ weight was 30 mg/g

II) Oxidability

The oxidation of the polyunsaturated fatty acid chains in the different preparations was next assessed. Rancidity would produce unpleasant fishy taste and smell. This could be at least partially circumvented by keeping the complex sealed under an inert atmosphere, and in an opaque container in absence of water. The oxidability of the different preparations was assessed by measuring peroxide value and anisidine values which reflects primary and secondary oxidations after 2 months (Table 6). 20 subjects (ten males and ten females) were asked for any taste or flavour of the 5 g samples suspended in 50 ml of apple juice.

TABLE 6

Oxidation of the preparations

| | peroxide value | | | anisidine value | | | | |
|---|---|---|---|---|---|---|---|---|
| Preparations | Number of samples | Mean | S.D. | Number of samples | Mean | S.D. | Taste and odor* | TOTOX |
| C | 6 | 5.26 | 1.77 | 6 | 9.88 | 1.41 | 16 | 20.5 |
| D | 6 | 2.77 | 0.17 | 6 | 7.12 | 1.02 | 7 | 6.4 |
| E | 6 | <1.0 | <1.0 | 6 | 2.20 | 0.28 | 1 | 3 |

Note*:
20 assays performed. The values indicate the number of assays where any unusual odor or taste was detected.

The microencapsulated omega-3 lipids could efficiently be mixed with nutrients to obtain an homogeneous formulation for the administration either in a sachet or capsule form. This same preparation in the sachet form is well protected from oxidation and does not on the short term develop any significant fish flavor.

Table 7 below presents compositions/formulations comprising different combinations of ingredients. To these preparations was added a few additive ingredients such as: antioxidants, flavorings or flavors (natural food). The recommended doses of the compositions are as indicated in Example 3.

TABLE 7

Representative formulations comprising omega-3 fatty acids

| Formulation | Form | Source Phospholipids | B6 (mg) | Mg (mg) | Zn/Cu (mg) | Omega-3 DHA/EPA (mg) | GLA (mg) | L-methyl folate (mg) |
|---|---|---|---|---|---|---|---|---|
| A | powder | Sediment (herring eggs) 100 mg | | | | — | | — |
| B | powder | Sediment (salmon eggs) 100 mg | | | | — | | — |
| C | powder | Sediment (herring eggs) 100 mg | 30 | 75 | 3.5/0.1 | 130/150 | | — |
| D | powder | Sediment (herring eggs) 100 mg | 30 | 75 | 3.5/0.1 | 134/153* | | — |
| E | powder in sachet | Sediment (herring eggs) 100 mg | 30 | 75 | 3.5/0.1 | 134/153* | | |
| F | Liquid form with Omega-3 emulsion | — | 30 | 75 | 3.5/0.1 | 134/153** | | |
| G | powder | Sediment (herring eggs) 100 mg | 30 | 75 | 3.5/0.1 | 134/153* | | |
| H | powder | | 30 | 75 | 3.5/0.1 | 134/153* | 100 | 0.4 mg |
| I | powder | | 60 | 150 | 7/0.2 | 268/306* | 100 | 0.4 mg |
| J | Liquid with Omega-3 emulsion | | 60 | 150 | 7/0.2 | 268/306* | 100 | 0.4 mg |

Preparation C is with cyclodextrin
GLA: Gamma Linolenic Acid
*In a complexed (cyclodextrin) or microencapsulated form
**in an emulsion form

EXAMPLE 5

Attenuation of ADHD Symptoms Using the Formulation D Described Herein

Stud A

A teenager suffering from Gilles de la Tourette syndrome and ADHD was hospitalized for three months in a psychiatric hospital. At that time, he was not able to function normally in all aspects of his life. In 2015, he was in fifth grade in a special class. Despite medication (Abilify™ 15 mg, Apo-Atomoxetine™ 25 mg, PMS-Clonazepam™ et Melatonin 3 mg), he had difficulty sustaining focus in school topics that require logic such as maths and language. He was also suffering from motor problems, having difficulties holding a pencil, or using scissors. Two weeks after being administered with formulation D of Table 7, the parents noticed that at least some of the symptoms of the disease already started to diminish. He had more energy, slept better and gained interest for school and sports. His grades at school were improved. His teachers were quite surprised by the changes. He started practicing martial arts and his life has significantly changed for the better. His parents summarised the results of the treatment by saying: this product has made miracle with our son.

Stud B

Two children of 9 and 12 years old diagnosed for ADHD symptoms by the psychologist of their school. The children were experiencing learning difficulties that were reflected in poor school grades and feedback from their teachers. The children were treated with the central nervous system stimulant methylphenidate (Ritalin®). The formulation D described in Example 4 was administered for 1 month. After one month of administration, the mother noticed improvements in the behavior of both children. Their teachers, which were not informed of the treatment, noted progress in their ability to concentrate by the second week, and has also noticed some improvements after 1 month (academic scores were improved by about 10%, as well as the general behaviour), and wondered what has happened with the children. The treatment with Ritalin® was maintained during the administration of formulation D. No noticeable adverse effects were associated with the use of this formula.

Stud C

The effect of formulation D was assessed a group of 13 adult volunteers. These individuals have not been previously identified as suffering from attention-deficit disorders. They were asked to give a general idea of their satisfaction of the product from the organoleptic and wellness viewpoints. A confidential survey based on the Canadian ADHD Resource Alliance (CADDRA) questionnaire to detect symptoms of ADHD (Adult ADHD Self-Report Scale (ASRS-v1.1) symptom checklist) consisting of 18 questions covering different aspects of behavior and cognition, was sent to the participants. They were invited to answer one of the following: rarely, sometimes, often or very often, at the outset (before use of formulation D) and after at least one month of use of formulation D (after treatment) to these 18 questions:

1. How often do you have difficulty finalizing the final details of a project once the most challenging parts have been done?
2. How often do you have trouble putting things in order when you have to do something that requires organization?
3. How often do you have difficulty remembering appointments or obligations?
4. When you need to do something that requires a lot of thought, how often do you avoid doing it or putting it off?
5. How often do you move or wiggle your hands or feet when you need to sit for an extended period of time?
6. How often do you feel excessively active and forced to do something, as if you were driven by an engine?
7. How often do you make careless mistakes when working on a boring or difficult project?
8. How often do you have difficulty concentrating when doing boring or repetitive work?
9. How often do you find it difficult to focus on what your interviewer is saying, even if he or she is talking to you directly?
10. At home or at work, how often do you misplace things or have trouble finding them?
11. How often do you become distracted by activity or noise around you?
12. How often do you leave your seat during meetings or other situations where you should remain seated?
13. How often do you have trouble keeping you quiet?
14. How often do you find it difficult to relax and rest in your free time?
15. How often do you over-talk during social gatherings?
16. During a conversation, how often do you finish the sentences of your interlocutors before they have time to finish them?
17. How often do you have trouble waiting for your turn when you should?
18. How often do you interrupt people when they are busy?

Participants were also asked to comment on the followings points:
A: When did you observe a change in behavior?
B. When did you notice a stable change in behavior?
C. Have there been any side effects? If yes,
   which ones?
   at what time during treatment?
   at what time of the day?
D. What do you think of the presentation of the product, the sachet?
E. What do you think of the smell and taste of the product?

Results—side effects and organoleptic properties. All the 13 participants persisted in taking the product. There were no clear side-effects during the study period. One participant reported an episode of diarrhea, which disappeared after a couple days. Three participants noticed a light fishy taste, but that did not bother them or affect compliance.

Results—responses to survey. Based on their responses, all of the individuals noticed some improvement in one or several aspects of their cognitive functions. At the end of the study period (one month), all participants were still taking the product. Compilation of scores are depicted in Tables 8a (onset) and 8b (after one month of use of formulation D).

TABLE 8a

Scores obtained before use of formulation D (onset)

| Question | P1 | P2 | P3 | P4 | P5 | P6 | P7 | P8 | P9 | P10 | P11 | P12 | P13 | Average |
|---|---|---|---|---|---|---|---|---|---|---|---|---|---|---|
| Q1  | 4 | 2 | 3 | 3 | 2 | 2 | 2 | 2 | 1 | 2 | 2 | 3 | 2 | 2.31 |
| Q2  | 4 | 1 | 3 | 3 | 2 | 3 | 3 | 2 | 1 | 1 | 2 | 2 | 2 | 2.23 |
| Q3  | 4 | 1 | 4 | 2 | 2 | 2 | 1 | 1 | 4 | 1 | 2 | 1 | 1 | 2.00 |
| Q4  | 4 | 1 | 3 | 3 | 3 | 2 | 1 | 2 | 1 | 2 | 2 | 2 | 2 | 2.15 |
| Q5  | 4 | 1 | 3 | 2 | 1 | 3 | 1 | 1 | 3 | 1 | 1 | 3 | 1 | 1.92 |
| Q6  | 3 | 1 | 3 | 4 | 1 | 2 | 1 | 2 | 3 | 2 | 2 | 2 | 2 | 2.15 |
| Q7  | 3 | 3 | 4 | 3 | 3 | 2 | 1 | 2 | 1 | 1 | 2 | 2 | 2 | 2.23 |
| Q8  | 4 | 3 | 3 | 2 | 2 | 3 | 2 | 1 | 3 | 2 | 2 | 2 | 1 | 2.31 |
| Q9  | 4 | 2 | 3 | 2 | 3 | 3 | 3 | 1 | 1 | 2 | 2 | 1 | 1 | 2.15 |
| Q10 | 4 | 2 | 3 | 3 | 2 | 2 | 1 | 2 | 3 | 2 | 1 | 1 | 2 | 2.15 |
| Q11 | 4 | 2 | 3 | 3 | 3 | 4 | 1 | 1 | 3 | 3 | 2 | 2 | 1 | 2.46 |
| Q12 | 2 | 1 | 3 | 3 | 1 | 1 | 1 | 2 | 1 | 1 | 2 | 2 | 2 | 1.69 |
| Q13 | 2 | 1 | 3 | 3 | 2 | 2 | 2 | 1 | 1 | 2 | 1 | 2 | 1 | 1.77 |
| Q14 | 2 | 1 | 3 | 3 | 3 | 1 | 1 | 2 | 1 | 2 | 2 | 2 | 2 | 1.92 |
| Q15 | 3 | 2 | 3 | 3 | 1 | 2 | 2 | 1 | 1 | 3 | 1 | 1 | 1 | 1.85 |
| Q16 | 3 | 1 | 3 | 3 | 3 | 4 | 1 | 1 | 2 | 3 | 1 | 1 | 1 | 2.08 |
| Q17 | 4 | 1 | 3 | 3 | 3 | 2 | 1 | 1 | 2 | 2 | 2 | 1 | 1 | 2.00 |
| Q18 | 4 | 1 | 3 | 3 | 2 | 1 | 1 | 1 | 1 | 1 | 1 | 1 | 1 | 1.62 |

TABLE 8b

Scores obtained after use of formulation D (one month)

| Question | P1 | P2 | P3 | P4 | P5 | P6 | P7 | P8 | P9 | P10 | P11 | P12 | P13 | Average |
|---|---|---|---|---|---|---|---|---|---|---|---|---|---|---|
| Q1 | 3 | 1 | 1 | 2 | 1 | 1 | 1 | 1 | 1 | 1 | 1 | 2 | 1 | 1.31 |
| Q2 | 3 | 1 | 1 | 2 | 1 | 2 | 1 | 1 | 1 | 1 | 1 | 1 | 1 | 1.31 |
| Q3 | 3 | 1 | 1 | 1 | 1 | 1 | 1 | 1 | 2 | 1 | 1 | 1 | 1 | 1.23 |

TABLE 8b-continued

Scores obtained after use of formulation D (one month)

| Question | P1 | P2 | P3 | P4 | P5 | P6 | P7 | P8 | P9 | P10 | P11 | P12 | P13 | Average |
|---|---|---|---|---|---|---|---|---|---|---|---|---|---|---|
| Q4  | 3 | 1 | 1 | 2 | 2 | 1 | 1 | 1 | 1 | 1 | 1 | 1 | 1 | 1.31 |
| Q5  | 2 | 1 | 1 | 2 | 1 | 3 | 1 | 1 | 3 | 1 | 1 | 2 | 1 | 1.54 |
| Q6  | 2 | 1 | 1 | 2 | 1 | 1 | 1 | 1 | 3 | 1 | 2 | 1 | 1 | 1.38 |
| Q7  | 2 | 1 | 1 | 2 | 1 | 1 | 1 | 1 | 1 | 1 | 1 | 1 | 1 | 1.15 |
| Q8  | 3 | 1 | 1 | 1 | 2 | 2 | 1 | 1 | 3 | 1 | 1 | 1 | 1 | 1.46 |
| Q9  | 3 | 1 | 1 | 1 | 2 | 2 | 2 | 1 | 1 | 1 | 2 | 1 | 1 | 1.46 |
| Q10 | 3 | 1 | 1 | 1 | 2 | 1 | 1 | 1 | 2 | 1 | 1 | 1 | 1 | 1.31 |
| Q11 | 3 | 1 | 1 | 1 | 2 | 3 | 1 | 1 | 2 | 1 | 1 | 1 | 1 | 1.46 |
| Q12 | 2 | 1 | 1 | 1 | 1 | 1 | 1 | 1 | 1 | 1 | 1 | 2 | 1 | 1.15 |
| Q13 | 2 | 1 | 1 | 1 | 2 | 1 | 2 | 1 | 1 | 1 | 1 | 2 | 1 | 1.31 |
| Q14 | 1 | 1 | 1 | 1 | 3 | 1 | 1 | 1 | 1 | 1 | 2 | 1 | 1 | 1.23 |
| Q15 | 1 | 2 | 1 | 1 | 1 | 2 | 1 | 1 | 1 | 1 | 1 | 1 | 1 | 1.15 |
| Q16 | 3 | 1 | 1 | 1 | 3 | 3 | 1 | 1 | 1 | 1 | 1 | 1 | 1 | 1.46 |
| Q17 | 3 | 1 | 1 | 1 | 2 | 2 | 1 | 1 | 1 | 1 | 1 | 1 | 1 | 1.31 |
| Q18 | 3 | 1 | 1 | 1 | 2 | 1 | 1 | 1 | 1 | 1 | 1 | 1 | 1 | 1.23 |

P1 to P13 correspond to the identification of the participant
Q1 to Q18: Questions 1 to 18 of the survey (see above)
Scores 1 to 4 indicates:
1 = rarely;
2 = sometimes;
3 = often;
4 = very often Based on testimonies from the participants, several conclusions may be drawn. Most of them reported an improvement with respect to the organisation and planning of their daily life (questions 1, 2, 4, 6, 7). Based on the responses to questions 7 to 12, some improvement in their capacity to concentrate or focus on a specific task was also observed. Statistical analysis (i.e. comparisons on matched data) of the results indicated that for most of the questions/symptoms tested (except for questions 3, 5, 13, 16 and 18), a significant beneficial effect or improvement of the symptoms was measured. These results provide further evidence that the use of formulation D may be useful to improve cognitive functions and to manage ADHD symptoms.

EXAMPLE 6

Incorporation of Formulation E into Different Beverages/Food Product

To simulate the use of a composition according to the invention by different users in different contexts, formulation E was incorporated to beverages/food product. The powder in sachet (formulation E) was opened and mixed with 150 to 300 ml of the following products: Milk, juice beverages, soft drinks, shakes, yogurt and water. The mixtures were tested twice. In all cases, the formulation mixed well in the media. Furthermore, there were no undesired tastes obtained.

EXAMPLE 7

Incorporation of Formulation F Into Different Beverages/Food Product

To determine if the formulation F in liquid form was stable, it was incorporated to 250 ml of fruit juices (2) and soft drink (1) (carbonated). The mixtures were tested just after mixing (fresh) and after two weeks in the beverages. No noticeable differences were observed between the fresh and the two-week samples, and no undesirable taste appeared during the two-week.

EXAMPLE 8

Attenuation of Depression Symptoms Using Formulation H Described Herein

A 45 years old nurse which was forced to quit her job because of a burn-out. It was her second burn-out in three years. She was prescribed the following medication by her physician: Effexor® (venlafaxine) 150 mg once-a-day, and Elavil® (amitriptyline) 10 mg for three months. She then started using formulation H described herein once-daily, after one month of using the formulation, she was able to reduce by half the dose of Effexor® and stopped Elavin®. After an additional 4 weeks on this regimen, she totally stopped the prescribed medication while continuing using formulation H. She was sufficiently well to return to her work and carry out her tasks normally.

The scope of the claims should not be limited by the embodiments set forth in the examples, but should be given the broadest interpretation consistent with the description as a whole.

REFERENCES

Patents and Applications

Beaudoin Adrien and Boudreault R. Method for preventing the oxidation of lipids in animal and vegetable oils and compositions produced by the method thereof. U.S. Pat. No. 8,404,875
Bruheim; Inge et al. Novel applications of omega-3 rich phospholipids U.S. Patent Application 20080058286 Mar. 6, 2008
Bruheim Inge et al Use of omega-3 rich phospholipids in the area of cognitive function. U.S. Patent Application. 20080070870 Mar. 20, 2008.

Non-Patent Documents

Akhondzadeh S, Mohammadi M R, Khademi M. Zinc sulfate as an adjunct to methylphenidate for the treatment of attention deficit hyperactivity disorder in children: a randomized double-blind and trial [ISRCTN64132371] .BMC Psychiatry. 2004 Apr. 8; 4 (1): 9.

Arnold L E, Pinkham S M, Votolato N. Does zinc moderate essential fatty acid and amphetamine treatment of attention deficit/hyperactivity disorder? *J Child Adolesc Psychopharmacol.* 2000; 10:111-117.

AP Association: Attention deficit hyperactivity disorder. In Diagnostic and Statistical Manual of Mental Disorders, Fourth Edition, Text Revision (DSM-IV-TR) Arlington, Va., American Psychiatric Association; 2000.

Bekaroglu M, Aslan Y, Gedik Y. Relationships between serum free fatty acids and zinc, and attention deficit hyperactivity disorder: a research note. *J Child Psychol Psychiatry.* 1996; 37(2):225-227.

Bélanger S A, Vanasse M, S Spahis, Sylvestre M P Lippe S, happy The F Ghadirian P Vanasse C M Levy E. Omega-3 fatty acid treatment of children with attention-deficit hyperactivity disorder: A randomized, double-blind, placebo controlled study. Paediatr Child Health. 2009; 14: 89-98.

Benerjee, A. K. Chomarod-latroscan TLC FID as an Analytical Technique Application in Lipid Analysis. Chemical AND ENVIRONMENTAL RESEARCH: 5, 1/4; 289-294.

Bhagavan et al., Cited in—other Nutritional and natural medical treatments for attention deficit/hyperactivity disorder—AD (H) D John V. Dommisse. Social Science Information, September 2000; flight. 39, 3: pp. 489-504.

Bjøorndal B., EI. Strand, J. Gjerde, P. Bohov, A. Svardal, B. W. K. Diehl, S. M. Innis, A. Berger and R. K Berge. Phospholipids from herring roe Improved plasma lipids and glucose tolerance in healthy young adults. Lipids in Health and Disease: 13:82, 1-8, 2014

Bilici M, Yildirim F, et al. Double-blind, placebo-controlled study of zinc sulfate in the treatment of attention deficit hyperactivity disorder. Prog. Neuropsychopharmacol. Biol. Psychiatry. 2004 January; 28 (1): 181-90.

G. E. Bledsoe, C. D. Bledsoe, and B. Rasco. Caviar and fish roe products. Critical Reviews in Food Science and Nutrition 43 (3): 317, 56, 2003. 29

Bligh, E. G., W. J. Dyer. A rapid method of total lipid extraction and purification. Review Canadian biochemistry and physiology: 37 (8): 911-917, 1959.

Boyle M H, Offord D R, Racine Y, M Sanford, Szatmari P, Fleming I: Evaluation of the original Ontario Child Health Study scales. Can J. Psychiatry 38: 397-405, 1993

Breton J J, L. Bergeron, Valla J P Berthiaume C, Gaudet N, J. Lambert, St Georges M., L Houde, Lepine S.: Quebec mental child health survey: prevalence of DSM-III-R mental health disorders. J. Child Psychol Psychiatry 40: 375-384, 1999

Finn R N, Østby G C, Norberg B Fyhn H J. In vivo oocyte hydration in Atlantic halibut (*Hippoglossus hippoglossus*); proteolytic release of free amino acids, and ion transport are driving force for osmotic water influx. J. Exp. Biol. 205: 211-224. 2002 European Journal of Clinical Investigation 35 (8): 499-507.

Fontani G, F Corradesci, Felici A, Alfatti F, R Bugarini, Fiaschi A I, Cerretani D, G Montorfano, Rizzo A M, Berra B.2005b. Blood profiles, body fat and mood state in healthy subjects is different supplemented diets with omega-3 polyunsaturated fatty acids. Eur J. Clin. Invest. 2005 August; 35(8):499-507.

Freund-Levi Y, Eriksdotter-Jonhagen M., Cederholm T., Basun H., Faxen Irving G., Garlind A., Vedin I., Vessby B., Wahlund L. O., Palmblad J. Omega-3 fatty acid treatment in 174 patients with mild to moderate Alzheimer disease: OmegAD study: a randomized double-blind trial. Archives of Neurology 63 (10): 1402-1408

Germano M., Domenico M., Montorfano G., Adorni L., Negroni M., Berra B., Rizzo A. M. Plasma, red blood cells phospholipids and clinical assessment after-long-chain omega-3 supplementation in children with attention deficit hyperactivity disorder (ADHD). Nutritional Neuroscience. 2007; 10: 1-9

Gow R. V., Sumich A., Vallee-Tourangeau F., Crawford M. A., Ghebremeskel K., Bueno A. A., Hibbeln J R, Taylor E., Wilson D. A., Rubia K. Omega-3 fatty acids are related to abnormal emotion processing in teenage boys with attention deficit hyperagressivity. Prostaglandins Leukot. Essential Fatty Acids. 2013 June; 88 (6): 419-29. doi: 10.1016/j.plefa.2013.03.008. E. pub 2013

Grøgaard, H. C. Extraction and analysis of marine lipids with emphasis on phospholipids evaluation and improvement of methods. Norwegian University of Science and Technology. Thesis: 2011.

Gustafsson P. A., Birberg-Thornberg U., DUCHEN K., Landgren M., Malmberg K., Pelling H., Strandvik B., Karlsson T. EPA supplementation improves teacher rated behavior and oppositional symptoms in children with ADHD. Acta Paediatr. 2010 October; 99(10):1540-9.

Mr. Haag. Essential fatty acids and the brain. Canadian Journal of Psychiatry 2003; 48 (3): 195-203.

Harding K. L., Judah R. D., Gant C.: Outcome-based comparison of Ritalin versus food-supplement Treated children with AD/HD. Altern. Med Rev.: 8: 319-330, 2003.

Harris W. S., Dayspring T. D., Moran T. J.: Omega-3 fatty acids and cardiovascular disease: new Developments and applications. Postgrad Med 125: 100-113, 2013

Higuchi T, Shirai N., Suzuki H.: Effects of dietary lipids herring roe on plasma lipid, glucose, insulin, and adiponectin concentrations in mice. J Agric. Food Chem. 54: 3750-3755. 2006

Hiramatsu, T. Matsubara, Mr. G. Weber, C. V. Sullivan and A. Hara c. Vitellogenesis in aquatic animals. Fisheries Science 68: 694-699. 2002

Hiramatsu N., and Hara. A. Relationship between vitellogenin and its related proteins in egg Shakalin taimen. Comp. Biochem Physiol: 115A, 243-251. 1996

Hirayama S., Hamazaki T., Terasawa K. Effect of docosahexaenoic acid-containing food administration on symptoms of attention-deficit/hyperactivity disorder—a placebo-controlled double blind study. Eur. J Clin. Nutr. 2004 March; 58 (3): 467-73.

Huss M., VoIP N., Strauss-Grabo Mr. Supplementation of polyunsaturated fatty acids, magnesium and zinc in children seeking medical advice for attention-deficit/hyperactivity problems—an observational cohort study. Lipids Health Dis 2010; 9: 105.

Ishikawa S., Ohtsuki S., Tomita K., Arihara K., Itoh M. "Protective effect of egg yolk phosvitin against ultraviolet-light-induced lipid peroxidation in the presence of iron ions. "Biol Trace Elem Res 105 (1-3): 249-56. 2005

Johnson M., Ostlund S., Fransson G, Kadesjo B., Gillberg C. Omega-3/omega-6 fatty acids for Attention deficit hyperactivity disorder: a randomized placebo-controlled trial in children and.adolescents. J. Atten Disord. 2009; 12: 394-401.

Kaitaranta J. K., and Ackman Robert G. Total lipids and lipid classes of fish roe. comparative Biochemistry and Physiology Part B: 69 (4): 725-729, 1981.

Kaushik, Pratibha, Dowling, Kim, Barrow, Colin J. and Adhikari, Benu 2015, Microencapsulation of omega-3 fatty acids: a review of microencapsulation and characterization methods, *Journal of functional foods*, vol. 19, no. Part B, pp. 868-881

Kirby A., Woodward A., Jackson S., Wang Y., Crawford M A. Childrens' learning and behavior and the cheek cell association with polyunsaturated fatty acid levels. Res. Dev. Disabil. 2010 May-June; 31 (3): 731-42.

Kolarevic J., Nerland A., Nilsen F., Finn R. N. Goldsinny wrasse (*Ctenolabrus rupestris*) is an extreme vtgAa deviation pelagophil teleost. Mol. Reprod. Dev. 75: 1011-1020.2008

Kozielec T.-Starobrat Hermelin B. Assessment of magnesium levels in children with Attention deficit hyperactivity disorder (ADHD). Magnes Res. 1997 June; 10 (2): 143-8. 31

Moriya H., Kuniminato T., Hosokawa Mr., Fukunaga K., Shiyama, and Miyashita K. Oxidative stability of salmon and herring roe and their dietary lipids effect on plasma cholesterol levels of rats. Fisheries Science: Vol. 73, Issue 3, 668-674, June 2007

Morris M. C., Evans D. A., Bienias J. L., Tangney C. C., Bennett D. A. Wilson R. S., Aggarwal N., Schneider J. Consumption of fish and n-3 fatty acid and risk of incident Alzheimer disease of. Archives of Neurology 2003; 60 (7): 940-946.

Millichap J G, Yee M M. The diet factor in attention-deficit/hyperactivity disorder. Pediatrics. 2012; 129(2):330-337.

Milte C. M., Sinn N., Buckley J. D., Coates A. M., Young R M., Howe P. R. Polyunsaturated fatty acids, cognition and literacy in children with ADHD with and without learning Difficulties. J Child Health Care 2011; 15: 299-311.

Mousain-Bosc M, Rock M., et al. Magnesium, Vit. B6 intake Reduces central nervous system hyperexcitability in children. J. Am. Coll. Nutr. 2004 October; 23 (5): 545S-548S.

Mousain-Bosc M. Improvement of neurobehavioral disorders in children Supplemented with magnesium-vitamin B6. I. Warning deficit hyperactivity disorders. Magnes Res. 2006 March; 19 (1): 46-52.

Al-Murad A. Holy and Barbara A. Rasco. "Characterization of Salmon (*Oncorhynchus Keta*) and Sturgeon (*Acipenser Transmontanus*) Caviar Proteins. "Journal of Food Biochemistry. Flight. 30, 4, 422-428, 2006

Nogovitsina O. R., Levitina E. V. [Effect of magnesium-B6 on the clinical and biochemical manifestations of the syndrome of attention deficit and hyperactivity in children] Eksp. Klin. Farmakol. 2006; January-February; 69 (1): 74-7. Russian.

Ohlendorf D. H., Wrenn R. F., and J. Banaszak L. Three-dimensional structure of the lipovitellin-phosvitin complex from amphibian oocytes. Nature. 1978; 272: 28-32.

Orbik O, Ozdag M F, Olgun A, Senol M G, Bek S, Akman S. Potential effects of zinc on information processing in boys with attention deficit hyperactivity disorder. *Prog Neuropsychopharmacol Biol Psychiatry.* 2008 Apr. 1; 32(3):662-667.

Prabakhara R. P. G., Balaswami K., Ypothirmayi T., Karuna M. L. S., Prasad. R. B. N.; Processing and Impact activating components in Food. Posted by Victor R. Preedy Chapter. 2014; 6. 463-468, Raldúa D, Fabr M., Bozzo M. G., Weber E., Cerda J. Cathepsin B-mediated protein degradation yolk during oocyte maturation killifish is blocked by an H+-ATPase inhibitor: effects on the hydration mechanism. Am. J. Physiol. Regul Integr. Comp. Physiol. 2006; 290: R456-66.

Richardson A. J., Puri B. K.: The potential role of fatty acids in attention-deficit/hyperactivity disorder. Essent. Fatty Acids. 2000; 63: 79-87.

Richardson A J, Puri Basant K. A double-blind randomized, placebo controlled study of the effects of supplementation with highly unsaturated fatty acids on ADHD-related symptoms in children with specific I earning difficulties. Progress in Neuro-Psychopharmacology & Biological Psychiatry. 2002; 26: 233-

Rowland A S, Lesesne C A, Abramowitz A J: The epidemiology of attention-deficit/hyperactivity disorder (ADHD): a public health view. Ment. Retard Dev. Disabil. Res. Rev. 2002; 8: 162-170.

Scahill L., Schwab-Stone M.: Epidemiology of ADHD in school-age children. Child Adolesc. Psychiatr. Clin. N. Am., 2000, 9: 541-55

Shahidi F. and Zhong Y. Lipid Oxidation: Measurement Methods. Published Online: 15 Jul. 2005: DOI: 10.1002/047167849X.bio050 Copyright @2005 John Wiley & Sons, Inc. (2005)

Sorgi P. J., Hallowell E. M., Hutchins H. L., Sears B. Effects of an open-label pilot study with high-dose EPA/DHA concentrates on plasma phospholipids and behavior in children with Attention deficit hyperactivity disorder. J. Nutr. 2007; 6: 16

Sinn N. Nutritional and dietary influences on attention deficit hyperactivity disorder. *Nutr Rev.* 2008 October; 66(10):558-68.

Starobrat-Hermelin, B., and Kozielec T. The effects of magnesium supplementation on physiological hyperactivity in children with ADHD: Positive response to magnesium oral loading test. Magnesium Research, 1997; 10, 149-156, Stevens, L. J., Zentall S. S., Abate M. L., Kuczek T., and Burgess, J. R.; Omega-3 fatty acids in boys with behavior, learning, and health problems, Physiology and Behavior. 1996; Vol. 59 (4-5), pp. 915-920.

Stevens L., Zhang W., Peck L., Kuczek T. N. Grevstad, Mahon A., Zentall S. S., Arnold L. E., Burgess J R. EFA supplementation in children with inattention, hyperactivity, and other Disruptive Behaviors. Lipids. 2003; 38: 1007-1021.

Stevenson, J., Buitelaar J, Cortese S., Ferrin M., Konofal E., Lecendreux M., Simonov E., Wong I. C. K., Sonuga-Barke E. Research Review: The role of diet in the treatment of attention-deficit/hyperactivity disorder—an appraisal of the evidence on efficacy and recommendations on the design of future studies. Journal of Child Psychology and Psychiatry. May 2014, Vol. 55, No. 5: 416-427

Tocher D. R., Sargent J. R., analysis of lipids and fatty acids in ripe roes of Some northwest European marine fish. Lipids, 19, 492-499. 1984

Tocher D. R., Fraser A. J, Sargent J. R., Gamble J. C.: Lipid class composition During embryonic and early larval development in Atlantic herring (*Clupea harengus*, L.). Lipids, 20, 84-89. 1985

Toren P., Sofia, E., Sela B. A., Wolmer L., Weitz R., Dov, I. Koren, S., Reiss A., Weizman R., and Laor N. (1996). Zinc deficiency in ADHD. Biol. Psychiatry, 40, 1308-1310.

Toren P, Eldar S, Sela B A, et al. Zinc deficiency in attention-deficit hyperactivity disorder. *Biol Psychiatry.* 1996; 40:1308-1310.

Transler C., Eilander A., Mitchell S., van de Meer N. The Impact of Polyunsaturated Fatty Acids in Reducing Child Attention Deficit Hyperactivity Disorders. J Atten. Disord. 2010 November; 14(3):232-46.

Vaisman N., Kaysar N., Zaruk-Adasha Y., Pelled D., Brichon G., Zwingelstein G., Bodennec J. Correlation between exchange in blood fatty acid composition and visual sustained attention to performance in children with inattention: effect of dietary n-3 fatty acids Containing phospholipids. Am J Clin Nutr. 2008; 87: 1170-1180.

Van de Rest O., Gleijnse J. M., Kok J. F., van Staveren W. A., Dullemeijer C., OldeRikkert M. G. M., Beekman A. T. F., Groot C. P. G. M. 2008. Effect of fish oil on cognitive performance in older subjects: a randomized controlled trial. Neurology 71 (6): 430-438.

Voigt R. G., Llorente A. M., Jensen C. L., Fraley J. K., Berretta M. C., and Heird W. C. A Randomized, Double-Blind, Placebo-Controlled Trial of Docosahexaenoic Acid Supplementation in Children with Attention Deficit/Hyperactivity Disorder, J. Pediatr. 2001; 139: 189-196.

Wahli W., Dawid I. B., Ryffel G. U., Weber R. Vitellogenesis and the vitellogenin gene family. Science. 1981; 212: 298-304.

Kwak H.-S. Nano- and Microencapsulation for Foods. Wiley-Blackwell; Oxford, UK: 2014.

Ahmad M., Madni A., Usman M., Munir A., Akhtar N., Khan H. S. Pharmaceutical micro encapsulation technology for development of controlled release drug delivery systems. WASET. 2011; 75:384-387.

Lam P., Gambari R. Advanced progress of microencapsulation technologies: In vivo and in vitro models for studying oral and transdermal drug deliveries. J. Control. Release. 2014; 178:25-35

Singh M., Hemant K., Ram M., Shivakumar H. Microencapsulation: A promising technique for controlled drug delivery. Res. Pharm. Sci. 2010; 5:65-77

Garg M., Wood L., Singh H., Moughan P. Means of delivering recommended levels of long chain n-3 polyunsaturated fatty acids in human diets. J. Food Sci. 2006; 71:R66-R71.

Taneja A., Singh H. Challenges for the delivery of long-chain n-3 fatty acids in functional foods. Annu. Rev. Food Sci. T. 2012; 3:105-123

Kolanowski W., Jaworska D., Weiβbrodt J., Kunz B. Sensory assessment of microencapsulated fish oil powder. J. Am. Oil Chem. Soc. 2007; 84:37-45

Kolanowski W., Ziolkowski M., Weiβbrodt J., Kunz B., Laufenberg G. Microencapsulation of fish oil by spray drying-impact on oxidative stability. Part 1. Eur. Food Res. Technol. 2006; 222:336-342.

Serfert Y., Drusch S., Schwarz K. Sensory odour profiling and lipid oxidation status of fish oil and microencapsulated fish oil. Food Chem. 2010; 123:968-975

Anwar S. H., Kunz B. The influence of drying methods on the stabilization of fish oil microcapsules: Comparison of spray granulation, spray drying, and freeze drying. J. Food Eng. 2011; 105:367-378.

Desai K. G. H., Jin Park H. Recent developments in microencapsulation of food ingredients. Dry Technol. 2005; 23:1361-1394.

Houhoula D. P., Oreopoulou V and Tzai C. A kinetic study of oil deterioration during frying and a comparison with heating. J. Amer. Oil Chem Soc. 2002; 79,133-137.

1. Papadopol V, Tuchendria E, Palamaru I: Magnesium and some psychological features in two groups of pupils (magnesium and psychic features). Magnes Res, 2001,14, 27-32.67

2. Wacker W E, Parisi A F: Magnesium metabolism. N Engl J Med, 1968, 278, 712-717

3. Held K, Antonijevic I A, Kunzel H, Uhr M, Wetter T C, Golly I C, Steiger A, Murck H: Oral $Mg^{2+}$ supplementation reverses age-related neuroendocrine and sleep EEG changes in humans. Pharmacopsychiatry, 2002, 35, 135-143

4. Eby G A, Eby K L, Murck H: Magnesium and major depression. In: Magnesium in the Central Nervous System. Eds. Vink R, Nechifor M, University of Adelaide Press, Adelaide, 2011, 313-330.

Phosphorus magnetic resonance spectroscopy seems to be currently the best tool for in vivo assessing magnesium level in the human brain [5)

5. lotti S, Malucelli E: In vivo assessment of Mg2+ in human brain and skeletal muscle by 31P-MRS. Magnes Res, 2008, 21, 157-162

6. Anna Serefko, Aleksandra Szopal, Piotr WlŸ, Gabriel Nowak, Maria Radziwoñ-Zaleska, Micha³ Skalski, Ewa Poleszak. Magnesium in depression: Pharmacological Reports 2013, 65, 547-554

7. Nechifor M: Magnesium in major depression. Magnes Res, 2009, 22, 163S-166S

8. Bernstein A L: Vitamin B6 in clinical neurology. Ann NY Acad Sci 1990; 585:250-260.

9. Stewart J W, Harrison W, Quitkin F, Baker H: Low B6 levels in depressed outpatients. Biol Psychiatry 1984; 19:613-616

10. DiGirolamo A M, Ramirez-Zea M: Role of zinc in maternal and child mental health. The American Journal of Clinical Nutrition 2009, 89(3):940S-945.

11. Lai J, Moxey A, Nowak G, Vashum K, Bailey K, McEvoy M: The efficacy of zinc supplementation in depression: Systematic review of randomised controlled trials. Journal of affective disorders 2012, 136(12):

12. Jacka F N, Maes M, Pasco J A, Williams L J, Berk M: Nutrient intakes and the common mental disorders in women. Journal of affective disorders 2012, 141(1):79-85.

13. Amani R, Saeidi S, Nazari Z, Nematpour S: Correlation Between Dietary Zinc Intakes and Its Serum Levels with Depression Scales in Young Female Students. Biological Trace Element Research 2010, 137(2):150-158

14. Yary T, Aazami S: Dietary Intake of Zinc was Inversely Associated with Depression. Biological Trace Element Research 2012, 145(3):286-290.

15. McLoughlin I J, Hodge J S: Zinc in depressive disorder. Acta Psychiatrica Scandinavica 1990, 82(6):451-453.

16. Szewczyk B, Poleszak E, Sowa-Kucma M, Siwek M, Dudek D, Ryszewska-Pokrasniewicz B, Radziwon-Zaleska M, Opoka W, Czekaj J, Pilc A et al: Antidepressant activity of zinc and magnesium in view of the current hypotheses of antidepressant action. Pharmacol Rep 2008, 60(5):588-589.

17. Sowa-Kuma M, Legutko B, Szewczyk B, Novak K, Znojek P, Poleszak E, Papp M, Pilc A, Nowak G: Antidepressant-like activity of zinc: further behavioral and molecular evidence. Journal of Neural Transmission 2008, 115(12):1621-1628.

18. Takeda A: Zinc Signaling in the Hippocampus and Its Relation to Pathogenesis of Depression. Molecular Neurobiology 2011, 44(2):166-174.

19. Maserejian N N, Hall S A, McKinlay J B: Low dietary or supplemental zinc is associated with depression symptoms among women, but not men, in a population-based epidemiological survey. Journal of affective disorders 2012, 136(3):781-788.

20. Massart R, Mongeau R, Lanfumey L. Beyond the monoaminergic hypothesis: neuroplasticity and epigenetic changes in a transgenic mouse model of depression. Philosophical Transactions of the Royal Society of London. Series B: Biological Sciences. 2012; 367(1601): 2485-2494.
21. Calder P C, Yaqoob P, Harvey D J, Watts A, Newsholme E A. Incorporation of fatty acids by concanavalin A-stimulated lymphocytes and the effect on fatty acid composition and membrane fluidity. Biochemical Journal. 1994; 300(2):509-518.
22. Lee C R, Hamm M W. Effect of dietary fat and cholesterol supplements on glucagon receptor binding and adenylate cyclase activity of rat liver plasma membrane. Journal of Nutrition. 1989; 119(4):539-546
23. Ahmad S N, Alma B S, Alam S Q. Dietary omega-3 fatty acids increase guanine nucleotide binding proteins and adenylate cyclase activity in rat salivary glands. The FASEB Journal. 1989; 3, article A948
24. Bowen R A, Clandinin M T. Dietary low linolenic acid compared with docosahexaenoic acid alter synaptic plasma membrane phospholipid fatty acid composition and sodium-potassium ATPase kinetics in developing rats. Journal of Neurochemistry. 2002; 83(4):764-774.
25. Vaidyanathan W, Rao K V, Sastry P S. Regulation of diacylglycerol kinase in rat brain membranes by docosahexaenoic acid. Neuroscience Letters. 1994; 179(1-2): 171-174.
26. Müller N, Schwarz M J. The immune-mediated alteration of serotonin and glutamate: towards an integrated view of depression. Molecular Psychiatry. 2007; 12(11): 988-1000.
27. Yan Q-S, Reith M E A, Jobe P C, Dailey J W. Dizocilpine (MK-801) increases not only dopamine but also serotonin and norepinephrine transmissions in the nucleus accumbens as measured by microdialysis in freely moving rats. Brain Research. 1997; 765(4149-158.
28. Martin P, Carlsson M L, Hjorth S. Systemic PCP treatment elevates brain extracellular 5-HT: a microdialysis study in awake rats. NeuroReport. 1998; 9(13):2985-2988.
29. Latour A, Grintal B, Champeil-Potokar G, et al. Omega-3 fatty acids deficiency aggravates glutamatergic synapse and astroglial aging in the rat hippocampal CA1. Aging Cell. 2013; 12(1):76-84
30. Grintal B, Champeil-Potokar G, Lavialle M, Vancassel S, Breton S, Denis I. Inhibition of astroglial glutamate transport by polyunsaturated fatty acids: evidence for a signalling role of docosahexaenoic acid. Neurochemistry International. 2009; 54(8):535-543.
31. Moreira J D, Knorr L, Ganzella M, et al. Omega-3 fatty acids deprivation affects ontogeny of glutamatergic synapses in rats: relevance for behavior alterations. Neurochemistry International. 2010; 56(6-7):753-759.
32. Speizer L A, Watson M J, Brunton L L. Differential effects of omega-3 fish oils on protein kinase activities in vitro. The American Journal of Physiology—Endocrinology and Metabolism. 1991; 261(1):E109-E114.
33. Holian O, Nelson R. Action of long-chain fatty acids on protein kinase C activity: comparison of omega-6 and omega-3 fatty acids. Anticancer Research. 1992; 12(3): 975-980.
34. Navarro C, Gonzalez-Alvarez I, Gonzalez-Alvarez M, et al. Influence of polyunsaturated fatty acids on Cortisol transport through MDCK and MDCK-MDR1 cells as blood-brain barrier in vitro model. European Journal of Pharmaceutical Sciences. 2011; 42(3):290-299.
35. Caraci F, Copani A, Nicoletti F, Drago F. Depression and Alzheimer's disease: neurobiological links and common pharmacological targets. European Journal of Pharmacology. 2010; 626(1):64-71.
36. Krishnan V, Nestler E J. Linking molecules to mood: new insight into the biology of depression. The American Journal of Psychiatry. 2010; 167(11):1305-1320
37. Wager-Smith K, Markou A. Depression: a repair response to stress-induced neuronal microdamage that can grade into a chronic neuroinflammatory condition? Neuroscience and Biobehavioral Reviews. 2011; 35(3): 742-764
38. Maes M, Yirmyia R, Noraberg J, et al. The inflammatory & neurodegenerative (I&ND) hypothesis of depression: leads for future research and new drug developments in depression. Metabolic Brain Disease. 2009; 24(1):27-53.
39. Myint A-M, Leonard B E, Steinbusch H W M, Kim Y-K. Th1, Th2, and Th3 cytokine alterations in major depression. Journal of Affective Disorders. 2005; 88(2):167-173.
40. Perry V H, Cunningham C, Holmes C. Systemic infections and inflammation affect chronic neurodegeneration. Nature Reviews Immunology. 2007; 7(2):161-167.
41. Tilley S L, Coffman T M, Koller B H. Mixed messages: modulation of inflammation and immune responses by prostaglandins and thromboxanes. Journal of Clinical Investigation. 2001; 108(1):15-23.
42. Kidd P M. Omega-3 DHA and EPA for cognition, behavior, and mood: clinical findings and structural-functional synergies with cell membrane phospholipids. Alternative Medicine Review. 2007; 12(3):207-227.
43. Calder PC. n-3 polyunsaturated fatty acids, inflammation, and inflammatory diseases. The American Journal of Clinical Nutrition. 2006; 83(supplement 6):S1505-S1519.
44. Peet M, Murphy B, Shay J, Horrobin D. Depletion of omega-3 fatty acid levels in red blood cell membranes of depressive patients. Biological Psychiatry. 1998; 43(5): 315-319.
45. Edwards R, Peet M, Shay J, Horrobin D. Omega-3 polyunsaturated fatty acid levels in the diet and in red blood cell membranes of depressed patients. Journal of Affective Disorders. 1998; 48(2-3):149-155
46. Maes M, Christophe A, Delanghe J, Altamura C, Neels H, Meltzer H Y. Lowered ω3 polyunsaturated fatty acids in serum phospholipids and cholesteryl esters of depressed patients. Psychiatry Research. 1999; 85(3):275-291.
47. Adams P B, Lawson S, Sanigorski A, Sinclair A J. Arachidonic acid to eicosapentaenoic acid ratio in blood correlates positively with clinical symptoms of depression. Lipids. 1996; 31(supplement 3):S157-S161
48. Maes M, Smith R, Christophe A, Cosyns P, Desnyder R, Meltzer H. Fatty acid composition in major depression: decreased omega 3 fractions in cholesteryl esters and increased C20: 4 omega 6/C20:5 omega 3 ratio in cholesteryl esters and phospholipids. Journal of Affective Disorders. 1996; 38(1):35-46.
49. Tiemeier H, van Tuijl H R, Hofman A, Kiliaan A J, Breteler M M B. Plasma fatty acid composition and depression are associated in the elderly: The Rotterdam Study. The American Journal of Clinical Nutrition. 2003; 78(1):40-46.
50. Kiecolt-Glaser J K, Belury M A, Porter K, Beversdorf D Q, Lemeshow S, Glaser R. Depressive symptoms, omega-6:omega-3 fatty acids, and inflammation in older adults. Psychosomatic Medicine. 2007; 69(3):217-224.
51. Rizzo A M, Corsetto P A, Montorfano G, et al. Comparison between the AA/EPA ratio in depressed and non 52. Rees A M, Austin M P, Owen C, Parker G. Omega-3 deficiency associated with perinatal depression: case control study. Psychiatry Research. 2009; 166(2-3):254-259.
53. Schins A, Crijns H J, Brummer R-J M, et al. Altered omega-3 polyunsaturated fatty acid status in depressed post-myocardial infarction patients. Acta Psychiatrica Scandinavica. 2007; 115(1):35-40.
54. Frasure-Smith N, Lespérance F, Julien P. Major depression is associated with lower omega-3 fatty acid levels in patients with recent acute coronary syndromes. Biological Psychiatry. 2004; 55(9):891-896.
55. Parker G B, Heruc G A, Hilton T M, et al. Low levels of docosahexaenoic acid identified in acute coronary syndrome patients with depression. Psychiatry Research. 2006; 141(3):279-286.
56. Sublette M E, Hibbeln J R, Galfalvy H, Oquendo M A, Mann J J. Omega-3 polyunsaturated essential fatty acid status as a predictor of future suicide risk. The American Journal of Psychiatry. 2006; 163(6):1100-1102
57. Riemer S, Maes M, Christophe A, Rief W. Lowered ω-3 PUFAs are related to major depression, but not to somatization syndrome. Journal of Affective Disorders. 2010; 123(1-3):173-180.
58. Mamalakis G, Tornaritis M, Kafatos A. Depression and adipose essential polyunsaturated fatty acids. Prostaglandins Leukotrienes and Essential Fatty Acids. 2002; 67(5): 311-318
59. Mamalakis G, Kalogeropoulos N, Andrikopoulos N, et al. Depression and long chain n-3 fatty acids in adipose tissue in adults from Crete. European Journal of Clinical Nutrition. 2006; 60(7):882-888.
60. Mamalakis G, Jansen E, Cremers H, Kiriakakis M, Tsibinos G, Kafatos A. Depression and adipose and serum cholesteryl ester polyunsaturated fatty acids in the survivors of the seven countries study population of Crete. European Journal of Clinical Nutrition. 2006; 60(8):1016-1023.
61. Mamalakis G, Kiriakakis M, Tsibinos G, et al. Lack of an association of depression with n-3 polyunsaturated fatty acids in adipose tissue and serum phospholipids in healthy adults. Pharmacology Biochemistry and Behavior. 2008; 89(1):6-10.
62. Mamalakis G, Kiriakakis M, Tsibinos G, Kafatos A. Depression and adipose polyunsaturated fatty acids in an adolescent group. Prostaglandins Leukotrienes and Essential Fatty Acids. 2004; 71(5):289-294.
63. Wichers M, Maes M. The psychoneuroimmuno-pathophysiology of cytokine-induced depression in humans. International Journal of Neuropsychopharmacology. 2002; 5(4):375-388.
64. Dowlati Y, Herrmann N, Swardfager W, et al. A meta-analysis of cytokines in major depression. Biological Psychiatry. 2010; 67(5):446-457.
65. Calder P C. N-3 fatty acids, inflammation and immunity: new mechanisms to explain old actions. Proceedings of the Nutrition Society. 2013; 72(3):326-336.66. Lu D Y, Tsao Y Y, Leung Y M, Su K P. Docosahexaenoic acid suppresses neuroinflammatory responses and induces heme oxygenase-1 expression in BV-2 microglia: implications of antidepressant effects for omega-3 fatty acids. Neuropsychopharmacology. 2010; 35(11):2238-2248.
67. Park Y, Moon H J, Kim S H. N-3 polyunsaturated fatty acid consumption produces neurobiological effects associated with prevention of depression in rats after the forced swimming test. Journal of Nutritional Biochemistry. 2011
68. Moranis A, Delpech J C, de Smedt-Peyrusse V, et al. Long term adequate n-3 polyunsaturated fatty acid diet protects from depressive-like behavior but not from working memory disruption and brain cytokine expression in aged mice. Brain, Behavior, and Immunity. 2012; 26(5): 721-731.
69. Serhan C N. Novel eicosanoid and docosanoid mediators: resolvins, docosatrienes, and neuroprotectins. Current Opinion in Clinical Nutrition and Metabolic Care. 2005; 8(2):115-121.
70. Farooqui A A, Horrocks L A, Farooqui T. Modulation of inflammation in brain: a matter of fat. Journal of Neurochemistry. 2007; 101(3):577-599.
71. Prescott S M, Stenson W F. Fish oil fix. Nature Medicine. 2005; 11(6):596-598.
72. Kim Y, Lee C. The gene encoding transforming growth factor β1 confers risk of ischemic stroke and vascular dementia. Stroke. 2006; 37(11):2843-2845.
73. Sutcigil L, Oktenli C, Musabak U, Bozkurt A, Cansever A, Uzun O, Sanisoglu S Y, Yesilova Z, Ozmenler N, Ozsahin A, Sengul A. Pro- and anti-inflammatory cytokine balance in major depression: effect of sertraline therapy. Clin Dev Immunol. 2007; 2007:76396.
74. Vollmar P, Haghikia A, Dermietzel R, Faustmann P M. Venlafaxine exhibits an anti-inflammatory effect in an inflammatory co-culture model. International Journal of Neuropsychopharmacology. 2008; 11(1):111-117.
75. Hida M, Fujita H, Ishikura K, Omori S, Hoshiya M, Awazu M. Eicosapentaenoic acid inhibits PDGF-induced mitogenesis and cyclin D1 expression via TGF-β in mesangial cells. Journal of Cellular Physiology. 2003; 196(2):293-300.
76. Thienprasert A, Samuhaseneetoo S, Popplestone K, West A L, Miles E A, Calder P C. Fish oil n-3 polyunsaturated fatty acids selectively affect plasma cytokines and decrease illness in Thai schoolchildren: a randomized, double-blind, placebo-controlled intervention trial. Journal of Pediatrics. 2009; 154(3):391-395.
77. Grosso, G., Galvano, F., Marventano, S., Malaguarnera, M., Bucolo C., Drago F., and Caraci F. Omega-3 Fatty Acids and Depression: Scientific Evidence and Biological Mechanisms Oxid Med Cell Longev. 2014; 2014: 313570.

The invention claimed is:
1. A homogenous solid composition consisting of:
about 250 mg to about 5000 mg of omega-3 fatty acid ethyl esters in solid form, wherein said omega-3 fatty acid ethyl esters are in the form of microencapsulated omega-3 fatty acids ethyl esters, and wherein the docosahexaenoic acid (DHA) ethyl ester/eicosapentaenoic acid (EPA) ethyl ester ratio in said omega-3 fatty acid ethyl esters is from 1/4 to 4/1;
about 10 mg to about 100 mg of vitamin B6;
about 75 mg to about 500 mg of magnesium in the form of a pharmaceutically acceptable salt;
at least 3.5 mg of zinc in the form of a pharmaceutically acceptable salt;
optionally at least 100 µg of copper in the form of picolinate, glycinate, orotate or gluconate;
optionally about 20 mg to about 200 mg of a sediment obtained by a method comprising:
(a) grinding fish roe or eggs in the presence of an antioxidant;

(b) submitting said fish roe or eggs to an osmotic shock at a temperature of less than about 10° C. for at least 20 minutes to obtain a lysed fish roe or egg mixture;

(c) sedimenting the mixture obtained in (b) at a temperature of less than about 10° C., thereby obtaining a supernatant fraction enriched in vitellogenin and a sediment fraction enriched in phospholipids;

(d) separating the supernatant fraction and sediment fraction by filtration or decantation; and (e) drying the sediment and coagulum at a temperature of about −30° C. to about 50° C.;

optionally about 50 mg to about 500 mg of gamma-linolenic acid (GLA);

optionally about 0.1 mg to about 1 mg of folic acid; and one or more pharmaceutically acceptable excipients.

2. The solid composition of claim 1, wherein the omega-3 fatty acid ethyl esters are present in an amount of about 250 mg.

3. The solid composition of claim 1 or 2, wherein said omega-3 fatty acid ethyl esters are in the form of microencapsulated omega-3 fatty acid ethyl esters obtained by complex coacervation.

4. The solid composition of claim 1 or 2, wherein said sediment is present in the composition.

5. The solid composition of claim 1, wherein about 50 mg to about 600 mg of said omega-3 fatty acid ethyl esters in solid form are eicosapentaenoic acid (EPA) ethyl esters.

6. A liquid composition consisting of:

about 250 mg to about 5000 mg of omega-3 fatty acid ethyl esters in liquid form, wherein said omega-3 fatty acids are microencapsulated omega-3 fatty acid ethyl esters, and wherein the docosahexaenoic acid (DHA) ethyl ester/eicosapentaenoic acid (EPA) ethyl ester ratio in said omega-3 fatty acids is from 1/4 to 4/1;

about 10 mg to about 100 mg of vitamin B6;

about 75 mg to about 500 mg of magnesium in the form of a pharmaceutically acceptable salt;

at least 3.5 mg of zinc in the form of a pharmaceutically acceptable salt;

optionally at least 100 μg of copper in the form of picolinate, glycinate, orotate or gluconate;

optionally about 20 mg to about 200 mg of a sediment obtained by a method comprising:

(a) grinding fish roe or eggs in the presence of an antioxidant;

(b) submitting said fish roe or eggs to an osmotic shock at a temperature of less than about 10° C. for at least 20 minutes to obtain a lysed fish roe or egg mixture;

(c) sedimenting the mixture obtained in (b) at a temperature of less than about 10° C., thereby obtaining a supernatant fraction enriched in vitellogenin and a sediment fraction enriched in phospholipids;

(d) separating the supernatant fraction and sediment fraction by filtration or decantation; and (e) drying the sediment and coagulum at a temperature of about −30° C. to about 50° C.;

optionally about 50 mg to about 500 mg of gamma-linolenic acid (GLA);

optionally about 0.1 mg to about 1 mg of folic acid; and one or more pharmaceutically acceptable excipients.

7. The liquid composition of claim 6, where the omega-3 fatty acid ethyl esters are present in an amount of about 250 mg.

8. The liquid composition of claim 6 or 7, wherein said omega-3 fatty acids are microencapsulated omega-3 fatty acid ethyl esters obtained by complex coacervation.

9. The liquid composition of claim 8, wherein about 50 mg to about 600 mg of said omega-3 fatty acid ethyl esters in solid form are eicosapentaenoic acid (EPA) ethyl esters.

10. A method for improving cognitive functions in a subject in need thereof, the method comprising administering to the subject an effective amount of the composition of claim 1 or 6.

11. The method of claim 10, wherein said subject suffers from a cognitive impairment.

12. The method of claim 10, wherein said subject suffers from attention-deficit/hyperactivity disorder (ADHD) or a neurodegenerative condition.

13. The method of claim 12, wherein said neurodegenerative condition is mild cognitive impairment, Alzheimer's disease or Parkinson's disease.

14. The composition of claim 1 or 6, wherein said gamma-linolenic acid (GLA) and/or folic acid are present in the composition.

15. A method for improving a symptom of a mood disorder in an adult subject comprising administering to said subject an effective amount of the composition defined in claim 14.

16. The method of claim 15, wherein said mood disorder is depression or anxiety.

17. The composition of claim 1, wherein the DHA/EPA ratio in said omega-3 fatty acids is from 2/3 to 3/2.

18. The composition of claim 6, wherein the DHA/EPA ratio in said omega-3 fatty acids is from 2/3 to 3/2.

19. The composition of claim 1, wherein the pharmaceutically acceptable salt of magnesium is magnesium picolinate, magnesium glycinate, or magnesium gluconate.

20. The composition of claim 6, wherein the pharmaceutically acceptable salt of magnesium is magnesium picolinate, magnesium glycinate, or magnesium gluconate.

21. The composition of claim 1, wherein the vitamin B6 is in the form of pyridoxine hydrochloride.

22. The composition of claim 6, wherein the vitamin B6 is in the form of pyridoxine hydrochloride.

23. The composition of claim 1, wherein the composition is for administration to a subject having one or more symptoms of a neurological condition.

24. The composition of claim 6, wherein the composition is for administration to a subject having one or more symptoms of a neurological condition.

25. The composition of claim 23, wherein the neurological condition is attention-deficit disorder (ADD), attention-deficit/hyperactivity disorder (ADHD), anxiety or depression.

26. The composition of claim 24, wherein the neurological condition is attention-deficit disorder (ADD), attention-deficit/hyperactivity disorder (ADHD), anxiety or depression.

* * * * *